United States Patent [19]

Carr et al.

[11] Patent Number: 4,483,988
[45] Date of Patent: Nov. 20, 1984

[54] SUBSTITUTED DERIVATIVES OF 4-T-ALKOXYCARBONYL-PIPERAZIN-2-ONES

[75] Inventors: Albert A. Carr; Robert A. Farr; John M. Kane, all of Cincinnati, Ohio

[73] Assignee: Richardson Merrell Inc., Cincinnati, Ohio

[21] Appl. No.: 399,554

[22] Filed: Jul. 19, 1982

Related U.S. Application Data

[60] Division of Ser. No. 130,431, Mar. 14, 1980, Pat. No. 4,341,698, which is a continuation-in-part of Ser. No. 50,950, Jun. 21, 1979, abandoned.

[51] Int. Cl.³ .................................... C07D 241/08
[52] U.S. Cl. .................................. 544/384; 424/250; 544/229; 544/374; 260/239 A; 260/112.5 R
[58] Field of Search ................ 544/384, 374, 229; 542/443

[56] References Cited

U.S. PATENT DOCUMENTS

| 4,079,137 | 3/1978 | Cyrus et al. | 424/250 |
| 4,167,512 | 9/1979 | Lai | 544/384 |
| 4,240,961 | 12/1980 | Lai | 544/384 |

FOREIGN PATENT DOCUMENTS 2438619A  2/1976  Fed. Rep. of Germany .

OTHER PUBLICATIONS

Moureu et al., "Bull. Soc. Chim., France", 1956, pp. 1785-1787.
Saikawa et al., "Chemical Abstracts", vol. 89, 1976, col. 89:75453w.

Primary Examiner—Glennon H. Hollrah
Assistant Examiner—James H. Turnipseed
Attorney, Agent, or Firm—Edlyn S. Simmons; Gary D. Street; William J. Stein

[57] ABSTRACT

Novel analgesic and antipsychotic agents having the formula

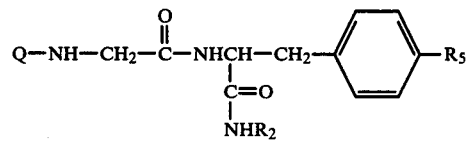

wherein Q is

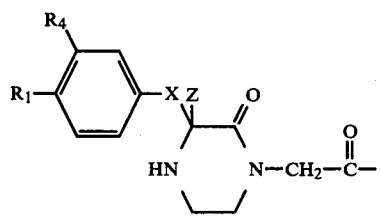

or

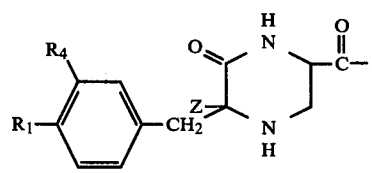

in which $R_1$ is hydrogen, hydroxy or halogen and $R_4$ is hydrogen or, $R_1$ and $R_4$ are both hydroxy; Z is hydrogen or straight chain lower alkyl having from 1 to 4 carbon atoms and X is methylene, carbonyl, hydroxymethylene, thio, sulfinyl or sulfonyl, or Z and X, taken together, are methylidenyl, with the proviso that when X is sulfonyl or sulfinyl, Z is other than hydrogen; $R_5$ is hydrogen or halogen, and $R_2$ is H, a straight or branched lower alkyl group having from 1 to 4 carbon atoms, the group

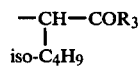

or the group

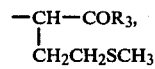

wherein $R_3$ is hydroxy, amino, alkylamino or dialkylamino wherein the alkyl moiety is straight or branched and has from 1 to 4 carbon atoms, diastereomers, enantiomers and pharmaceutically acceptable salts thereof.

6 Claims, No Drawings

SUBSTITUTED DERIVATIVES OF 4-T-ALKOXYCARBONYL-PIPERAZIN-2-ONES

This is a divisional of application Ser. No. 130,431, filed Mar. 14, 1980, now U.S. Pat. No. 4,341,698, which is a continuation-in-part of application Ser. No. 50,950, filed June 21, 1979, abandoned.

FIELD OF INVENTION

This invention relates to novel enkephalin derivatives which are pharmaceutically useful compounds.

SUMMARY OF INVENTION

Compounds of the following general Formula I and the diastereomers thereof are useful as analgesics in the alleviation of pain.

Formula I

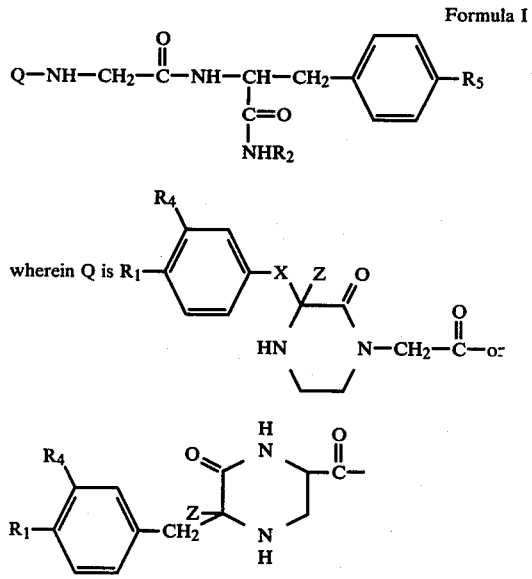

in which $R_1$ is hydrogen, hydroxy or halogen and $R_4$ is hydrogen or $R_1$ and $R_4$ are both hydroxy; Z is hydrogen or straight chain lower alkyl of from 1 to 4 carbon atoms and X is methylene, carbonyl, hydroxymethylene or thio, Z is alkyl and X is sulfinyl or sulfonyl, or Z and X, taken together, form a methylidene group; $R_5$ is hydrogen or halogen; and $R_2$ is H, a straight or branched lower alkyl group having from 1 to 4 carbon atoms, the group

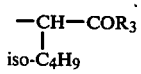
—CH—COR$_3$
|
iso-C$_4$H$_9$ or the group

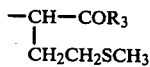
—CH—COR$_3$
|
CH$_2$CH$_2$SCH$_3$ wherein $R_3$ is hydroxy, amino, alkylamino or dialkylamino wherein the alkyl moiety is straight or branched and has from 1 to 4 carbon atoms.

The individual diastereomers and enantiomers of the compounds of Formula I and novel intermediates for the preparation of the compounds of Formula I are also a part of this invention.

Compounds of Formula I wherein either of $R_1$ and $R_5$ is halogen and especially those wherein both $R_1$ and $R_5$ are halogen are additionally active as neuroleptic tranquilizers, useful as antipsychotic agents.

DETAILED DESCRIPTION OF INVENTION

As used herein the term lower alkyl or alkyl is taken to mean a straight or branched alkyl group having from 1 to 4 carbon atoms, except that when Z is lower alkyl, only straight chain alkyl groups are employed. Preferred compounds of Formula I include those wherein $R_2$ is methyl, ethyl or n-propyl and those wherein $R_3$ is methyl-, ethyl-, or n-propylamino.

The term halogen is taken to mean fluorine, chlorine or bromine. The preferred halogen for use in compounds of Formula I is fluorine.

The term methylene refers to the divalent moiety of structure —CH$_2$—. The term carbonyl refers to the divalent moiety of structure

The term hydroxymethylene refers to the divalent moiety of structure

The term thio refers to a divalent sulfur atom, —S—. The term sulfinyl refers to the divalent moiety of structure

The term sulfonyl refers to the divalent moiety of structure

The term methylidene refers to the trivalent moiety —CH=. When X and Z are combined to form the methylidene radical, the double bond of the methylidene moiety is attached to the piperazine ring.

Preferred compounds of Formula I are those wherein X is methylene and Z is hydrogen. Preferred analgesics of Formula I are those compounds of Formula I wherein $R_1$ is hydroxy and $R_5$ is hydrogen. Preferred neuroleptic tranquilizers of Formula I are those compounds of Formula I wherein $R_1$ and $R_5$ are fluorine.

This invention also includes pharmaceutically acceptable salts of the compounds of Formula I. Pharmaceutically acceptable acid addition salts of the compounds of this invention are those of any suitable inorganic or organic acid. Suitable inorganic acids are, for example, hydrochloric, hydrobromic, sulfuric, and phosphoric acids. Suitable organic acids include carboxylic acids, such as acetic, propionic, glycolic, lactic, pyruvic, malonic, succinic, fumaric, malic, tartaric, citric, cyclamic, ascorbic, maleic, hydroxymaleic and dihydroxymaleic, benzoic, phenylacetic, 4-aminobenzoic, 4-hydroxybenzoic, anthranilic, cinnamic, salicyclic, 4-aminosalicylic, 2-phenoxybenzoic, 2-acetoxybenzoic, and mandelic acid, and sulfonic acids, such as methanesulfonic, ethanesulfonic and β-hydroxyethanesulfonic acid. Non-toxic salts of the appropriate carboxy containing compounds of Formula I formed with inorganic or organic bases are also included within the scope of this invention and include, for example, those of alkali metals such as sodium, potassium and lithium, alkaline earth metals, for example, calcium and magnesium, light metals of group IIIA, for example, aluminum, organic amines, such as primary, secondary or tertiary amines, for example, cyclohexylamine, ethylamine, pyridine, methylaminoethanol and piperazine. The salts are prepared by conventional means as, for example, by treating a compound of Formula I with an appropriate acid, or when $R_3$ is OH, an appropriate base.

As analgesic agents the compounds of Formula I and diastereomers thereof are useful in alleviating pain. Compound of Formula I wherein $R_1$, $R_5$ or both $R_1$ and $R_5$ are halogen and the individual diastereomers thereof are additionally useful as neuroleptic tranquilizers. Neuroleptic tranquilizers are useful for treatment of patients showing symptoms of psychoses, such as schizophrenia, or of severe anxiety, agitation or aggressiveness. Such agents have a tranquilizing effect on psychomotor activity, inducing a state of general quiescence in the patient without inducing sleep.

The compounds may be administered alone or in the form of a pharmaceutical preparation to a patient in need of treatment.

As used herein the term patient is taken to mean a warm blooded animal, such as mammals, for example, cats, dogs, pigs, horses, cows, sheep, humans, guinea pigs, mice and rats.

The compounds are administered in any effective amount either orally or parenterally, for example, intravenously, intramuscularly, subcutaneously or intracerebroventricularly (icv). For oral administration, the effective amount of compound will vary from about 10 to 500 mg/kg of body weight of the patient per day, preferably 10 to 200 mg/kg. For parenteral administration other than icv the effective amount of compound will vary from about 0.1 to 100 mg/kg of body weight of the patient per day, preferably 0.1 to 25 mg/kg. For icv administration, the effective amount of compound will vary from about 0.1 to 10 μg/kg per day. A typical unit dosage for oral administration may contain from 10 to 200 mg of active ingredient; for parenteral administration other than icv, a typical unit dosage form may contain 10 to 50 mg of active ingredient. For icv administration, a typical unit dosage form may contain 0.5 to 5 μg.

As indicated hereinabove, the compounds of the present invention are useful as analgesics. The compounds of the invention can be used in the same manner as met-enkephalin, leu-enkephalin and D-alanyl[2]-metenkephalin.

The compounds of the present invention offer advantages over the above-enumerated known enkephalins in that the piperazinone moiety is more stable to proteolysis than the N-terminaldipeptide moiety of the known enkephalins, resulting in a longer half-life under physiological conditions.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases, such as lactose, sucrose or corn starch, in combination with binders, such as acacia, corn starch or gelatin, disintegrating agents, such as corn starch, potato starch or alginic acid, and a lubricant, such as stearic acid or magnesium stearate. An enteric coated solid unit dosage form is also suitable for use in practicing the present invention. For example, a tableted formulation of a compound of Formula I could be provided a laminated coating that would be resistant to gastric juice.

For parenteral administration the compounds may be administered as injectable dosages of a solution or suspension of the compound in a physiologically acceptable diluent with a pharmaceutical carrier which can be a sterile liquid, such as water and oils, with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, ethanol, and glycols, such as propylene glycol or polyethylene glycol, are preferred liquid carriers, particularly for injectable solutions.

The compounds can be administered in the form of a depot injection or implant preparation which may be formulated in such a manner as to permit a sustained release of the active ingredient. The active ingredient, together with a suitable carrier, can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

The salts of the compounds of Formula I show the analgesic and antipsychotic utility described hereinabove and are a part of the present invention.

The compounds of general Formula I are prepared by coupling a blocked derivative of a 2-piperazinone-1-acetic acid of the formula

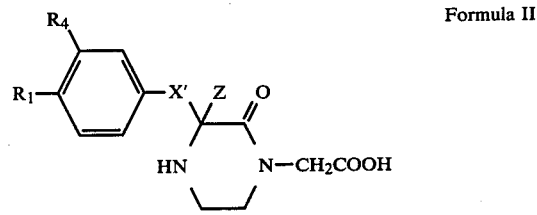

Formula II or of a 6-piperazinone-2-carboxylic acid of the formula

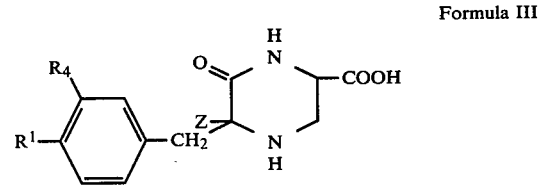

Formula III with a dipeptide or tripeptide of the formula

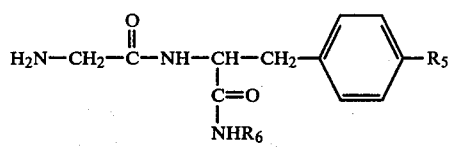

Formula IV wherein R$_6$ is hydrogen, a straight or branched lower alkyl group having from 1 to 4 carbon atoms, the group

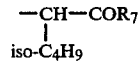

or the group

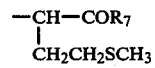

wherein R$_7$ is —OCH$_3$, amino, alkylamino or dialkylamino, wherein the alkyl moiety is straight or branched and has from 1 to 4 carbon atoms, X' is methylene, thio, carbonyl, blocked carbonyl or blocked hydroxymethylene, or if Z is alkyl, sulfinyl or sulfonyl, or together with Z, is methylidene, and R$_1$, R$_4$, R$_5$ and Z have the meanings defined hereinabove; followed by removal of the blocking groups.

Suitable blocking groups for the protection of the nitrogen atom in the 4-position of the piperazinone moiety are well known in the art and include, for example, tertiaryalkoxycarbonyl groups, such as tertiary butoxycarbonyl (t-boc) and amyloxycarbonyl, benzyloxycarbonyl and substituted benzyloxycarbonyl groups, cycloalkoxycarbonyl groups, and vinyloxycarbonyl groups. Suitable reagents and reaction conditions for the blocking and deblocking of nitrogen atoms are described by M. Bodanszky et al., in *Peptide Synthesis*, 2nd Edition (John Wiley and Sons) p.18–49 (1976) and by R. Olofson et al., in U.S. Pat. No. 3,905,981, which are hereby incorporated by reference. The preferred nitrogen blocking group is tertiary butoxycarbonyl.

Suitable blocking groups for the protection of hydroxy substituents present when X is CHOH or R$_1$ is hydroxy are also well known in the art and include the benzyl, methyl and tertiary butyl groups, trialkylsilyl groups, such as t-butyldimethylsilyl, alkoxyalkyl groups, such as methoxymethyl or (2-methoxyethoxy)-methyl (MEM), and tetrahydropyranyl. Suitable reagents and reaction conditions for the blocking and deblocking of hydroxy groups are described by M. Bodanszky et al., op. cit., p.59–60 and by E. Schroder and K. Lubke in *The Peptides*, Vol. I (Academic Press, N.Y.) p.222–226 (1965). The preferred blocking group for the protection of the phenolic hydroxy substituent is benzyl. The preferred blocking for the protection of the hydroxymethylene moiety is (2-methoxyethoxy)-methyl.

Suitable blocking groups for the carbonyl moiety include ketals and hydrazones. Methods for conversion of ketones to ketals and hydrazones and for regeneration of the ketone are well known in the art.

The ester moiety present when R$_7$ is OCH$_3$ is also cleaved by well known methods to yield acids of Formula I or reacted with ammonia or a primary amine to give amides of Formula I.

The reaction of the abovedescribed blocked derivative of either Formula IIA or Formula IIIA

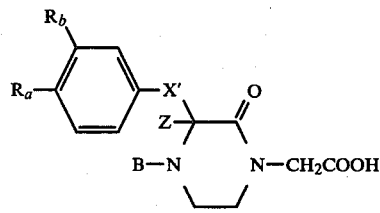

Formula IIA

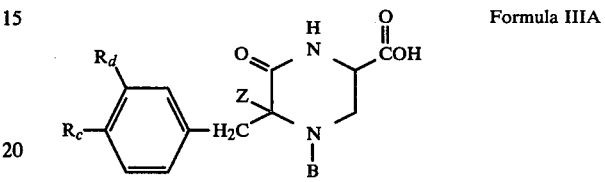

Formula IIIA wherein R$_a$ or R$_c$ is hydrogen, blocked hydroxy or halogen and R$_b$ and R$_d$ is hydrogen, or R$_a$ and R$_b$ or R$_c$ and R$_d$ are both blocked hydroxy, B is a suitable N-blocking group, and X' and Z have the meanings defined above, with compounds of Formula IV is carried out at temperatures of about −10° C. to 25° C. for about ½ hours to 24 hours in a suitable solvent such as anhydrous tetrahydrofuran (THF), chloroform, methylene chloride or dioxane. When R$_7$ is —OCH$_3$, subsequent to the coupling of a compound of Formula IIA or IIIA with a compound of Formula IV, the product obtained is hydrolyzed to remove the methyl ester using, for example, lithium hydroxide followed by treatment with cold and dilute hydrochloric acid, or converted to an amide by reaction with ammonia or with an alkyl- or dialkylamine. When R$_a$ or R$_c$ is blocked hydroxy, the blocking group is removed by standard methods; for example, when R$_a$ or R$_c$ is benzyloxy, the benzyl group may be removed by catalytic hydrogenation or by treatment with hydrogen fluoride, for example by reaction with pyridine-HF in THF at 0° C. to 50° C. in the presence of a scavenger, such as anisole, or when X' is MEM-blocked —CHOH—, the methoxyethoxymethyl group may be removed by reaction with trifluoroacetic acid at a temperature of from 0° C. to 25° C. in a suitable solvent, such as CH$_2$Cl$_2$. The nitrogen blocking group, B, is removed by standard methods; for example, the tertiary butoxycarbonyl group is removed by treatment with trifluoroacetic acid (TFA) at 0° C. to 25° C., by treatment with gaseous HCl in methanol or ether for 10 to 30 minutes, as described above. When blocked hydroxy is present, acid sensitive N- and OH- blocking groups are cleaved simultaneously by HF or TFA. When X' is a ketal, the corresponding compound of Formula I wherein X is carbonyl may be formed by reacting the ketal with aqueous acid. Ketal removal under acid conditions may take place simultaneously with removal of a tertiary alkoxycarbonyl nitrogen blocking group. When X' is, for example, dialkyl hydrazone, the compound of Formula I wherein X is carbonyl may be formed by reaction of the hydrazone with copper acetate in water and THF according to the method generally described by E. J. Corey, et al., in *Tetrahedron Letters* 1976, p.3667.

The compounds of Formula IV are prepared by coupling an N-blocked glycine, for example, N-t-boc-glycine, that is, glycine wherein the nitrogen atom is protected with tertiary butoxycarbonyl, with a lower alkyl, for example, methyl, ester of $R_5$-substituted-phenylalanine, to give a lower alkyl ester of the compound of Formula V, wherein R' is lower alkyl which may be hydrolyzed with, for example, lithium hydroxide, then acidified with cold and dilute hydrochloric acid to give the acid, wherein R' is hydrogen.

is hydroxymethylene or carbonyl, to yield an unblocked compound of Formula I.

Alternatively, a compound of Formula I may be prepared by forming a peptide bond between the compound of Formula IIA or IIIA and a glycine ester and subsequently reacting the product to form additional peptide bonds with $R_5$-substituted phenylalanine and then with a compound of formula $H_2NR_6$, and deblocking, according to standard well-known procedures.

Compounds of Formula IIA are prepared by means of the alkylation of the dianion formed upon metallation of a 4-tertiaryalkoxycarbonyl-2-piperazinone according to general Reaction Scheme I:

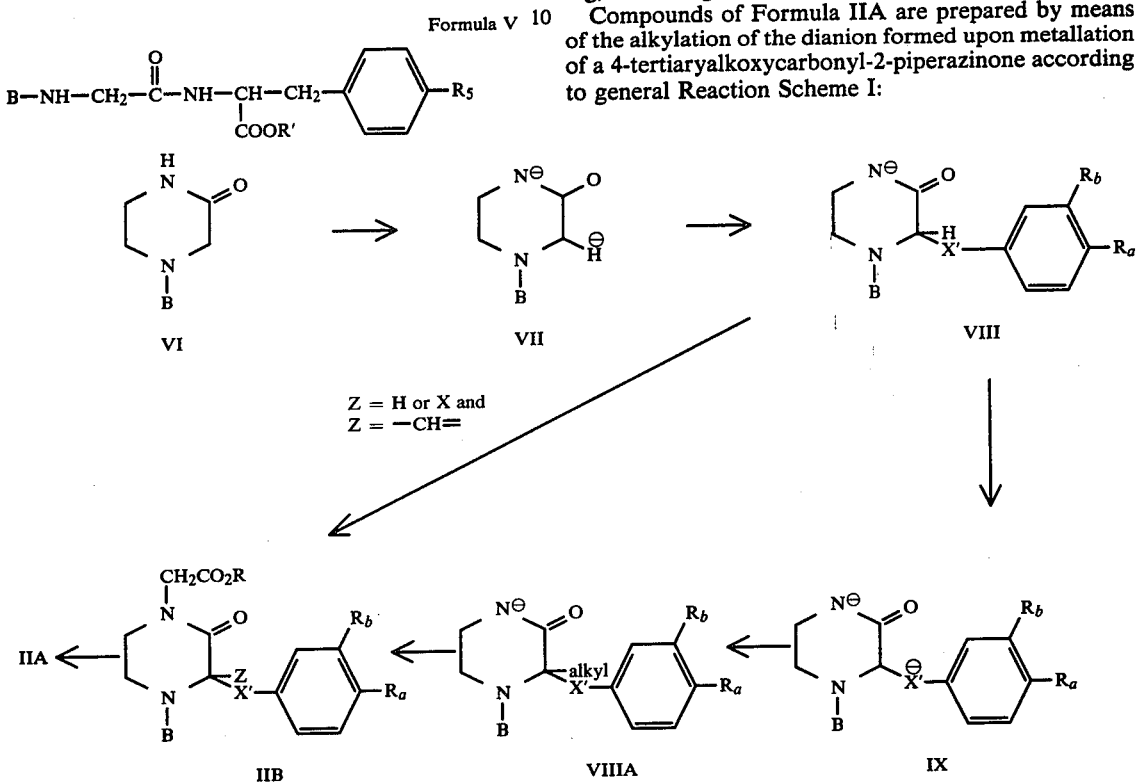

When $R_6$ in Formula IV is hydrogen or straight or branched lower alkyl, the ester of Formula V may be reacted directly with ammonia or a lower alkyl amine to give the compound of Formula IV wherein $R_6$ is hydrogen or lower alkyl, respectively.

The acid of Formula V may be reacted with a suitable coupling reagent and coupled with an amine of formula $H_2NR_6$, wherein $R_6$ has the meaning defined in Formula IV, above. Suitable chemical procedures for the coupling of amino acid are standard well-known procedures, for example, the mixed anhydride procedure as generally described by J. Matsoukas et al., J. Org. Chem. 42, 2105 (1977), or by any of the procedures described by M. Bodanszky et al., op. cit., p.85–136, hereby incorporated by reference.

Exemplary coupling reagents include 1-ethoxycarbonyl-2-ethoxy-1,2-dihydroquinoline (EEDQ), acid chlorides, such as pivaloyl chloride and isobutylchloroformate, 3-alkyloxazolidine-2,5-diones, 1,1'-carbonyldiimidazole, and carbodiimides, such as dicyclohexylcarbodiimide.

The coupling reaction is followed by removal of the nitrogen blocking group, for example, by treatment with TFA or gaseous HCl as generally described hereinabove, and of hydroxy and ketone blocking groups which may be present when $R_1$ is hydroxy and when X Piperazinone is reacted with a blocking reagent, preferably a tertiary alkoxycarbonyl blocking reagent, such as 2-(t-butoxycarbonyloxyimino)-2-phenyl acetonitrile (BOC-ON), t-butoxycarbonylazide, or t-amyl chloroformate, in the presence of an anhydrous solvent, such as tetrahydrofuran, dimethoxyethane (DME), chloroform, 1,2-dichlorobenzene, or toluene, at a temperature of from 0° C. to the boiling point of the solvent, preferably at room temperature, for from about ½ hour to 18 hours, preferably about 2 hours, to yield a blocked piperazinone of Formula VI, wherein B is a blocking group, preferably tertiary alkoxycarbonyl.

The dianion of Formula VII is generated by reaction of the blocked piperazinone of Formula VI with a slight excess over 2 equivalents, preferably about 2.2 equivalents, of a dianion-generating strong base, selected from an alkali metal amide, such as sodium amide, and a dialkylamino lithium, such as diethylamino lithium, dicyclohexylamino lithium or, preferably, diisopropylaminolithium, which is generated in situ by reaction of an alkyl lithium, such as n-butyl lithium, with a dialkylamine, such as diisopropylamine. The piperazinone of Formula VI is reacted with the base in the presence of an ether solvent, such as diethylether, THF, DME, 1,4-dioxane or diglyme, at a temperature of from −40° C. to 20° C., preferably about 0° C., for from about 1 to 5 hours, preferably about 3 hours, yielding a dianion of Formula VII.

A suitable electrophilic reagent is added to the reaction mixture and stirred for an additional 1 to 24 hours, preferably about 4 hours, at from 0° C. to 50° C., preferably at room temperature, to yield a monoanion substituted in the 3-position by the group,

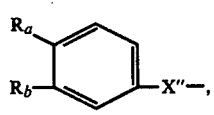

which may be worked up according to standard methods to yield a compound of general formula

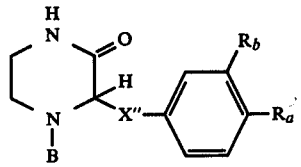
Formula VIIIB wherein X'' is methylene, carbonyl, hydroxymethylene, thio, sulfinyl or sulfonyl.

The purified compound of Formula VIIIB may be reacted with a suitable protecting reagent when X is carbonyl or hydroxymethylene or dehydrated when X'' in Formula VIIIB is hydroxymethylene and a compound of Formula I wherein X and Z together are methylidene, is desired. When Z is other than lower alkyl, the protected compound of Formula VIIIB wherein X'' is methylene, thio, protected carbonyl, protected hydroxymethylene or methylidene is reacted with a slight excess, preferably about 1.1 equivalents of a strong base, such as those named above, lithium or sodium hydride, or sodium hexamethyldisilazane, in the presence of a suitable solvent, for from 3 to 30 hours, preferably about 8 hours, at a temperature of −40° C. to 20° C., preferably about 0° C., generating the monoanion of Formula VIII, which is then reacted with a lower alkyl ester, preferably the methyl ester, of an α-haloacetic acid of formula

halo—CH₂—COOR wherein halo is chloro, bromo or iodo, and R is lower alkyl, and again stirred for from 1 to 24 hours at about 0° C. to 50° C. to yield an ester of Formula IIB, which is hydrolyzed according to standard methods, for example, by reaction with aqueous lithium hydroxide in a lower alcohol solvent for from 1/20 to 4 hours, preferably about ½ hour, to yield an N⁴-protected-3-substituted-2-oxo-1-piperazineacetic acid of Formula IIA, wherein Z is hydrogen.

When Z is straight chain lower alkyl, the compound of Formula VIIIB, which is protected when X is hydroxymethylene, is reacted with an additional 2.2 equivalents of a dianion-generating base, as described hereinabove, to generate the dianion of the Formula IX, and the dianion reacted with an alkyl halide, such as methyl iodide or ethyl chloride, to yield the 3,3-disubstituted monoanion of structure VIIIA, which is worked up to give a compound of Formula VIIIC,

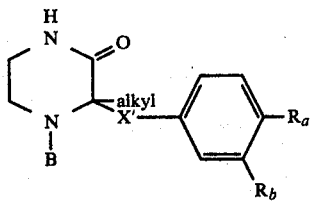
Formula VIIIC which is reacted with a slight excess over 1 equivalent of strong base and reacted with an α-haloacetic acid ester, as described above, and hydrolyzed to yield an N⁴-protected-3,3-disubstituted 2-oxo-1-piperazineacetic acid of Structure IIA.

Alternatively, the reaction sequence may be performed without interruption. A monoanion of Formula VIII wherein X' is methylene or thio, which is produced by the reaction of an electrophilic reagent with dianion VII, may be reacted without isolation with the α-haloacetic acid ester to give a compound of Formula IIB wherein Z is H. A monoanion of Formula VIII wherein X' is methylene, thio, carbonyl, sulfinyl or sulfonyl, may be reacted without isolation with 1.1 equivalents of strong base, as described hereinabove, and the resulting dianion of formula IX alkylated sequentially by an alkyl halide and an α-haloacetic acid to give the compounds of Formula IIB wherein Z is alkyl.

Suitable electrophilic reagents for preparation of compounds of Formula IIA wherein X' is methylene are benzyl halides of formula

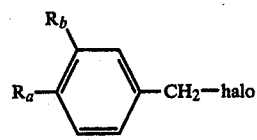

wherein halo is bromine, chlorine or iodine and $R_a$ and $R_b$ have the meanings defined above. The benzyl halides are well known compounds which are commercially available or may be prepared by art recognized methods.

Suitable electrophilic reagents for the preparation of compounds of Formula IIA wherein X' is carbonyl are benzoyl halides of formula

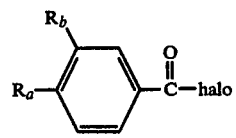

and benzoate esters of formula

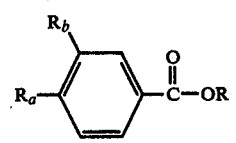

wherein $R_a$, $R_b$ and halo have the above-defined meanings and R is lower alkyl. The benzoyl halides and benzoate esters are well-known compounds which are commercially available or may be prepared by art recognized methods.

When X is carbonyl and Z is hydrogen, it is necessary to block the carbonyl moiety of a ketone, Formula VIIIB with a carbonyl protecting reagent before attempting to alkylate the 1-nitrogen atom of the piperazine ring. For example, a cyclic ketal may be formed by reacting the ketone with an alkyleneglycol of from 2 to 8, preferably 2 to 5 carbon atoms, having 2 or 3 carbon atoms in the chain linking the 2 hydroxy groups, in a solvent, such as benzene or toluene in the presence of p-toluenesulfonic acid, for from 12 to 72 hours, removing the water generated by the reaction azeotropically, typically by use of Dean-Stark trap. Exemplary alkylene glycols are 1,2-ethanediol, which converts the carbonyl moiety to ethylenedioxymethylene, and 2,2-dimethyl propane-1,3-diol, which converts the carbonyl moiety to 2,2-dimethylpropylenedioxymethylene. Similarly, a dialkyl ketal may be formed by reaction of the ketone with a lower alkyl ester of orthoformic acid in the presence of an alcohol solvent, such as methanol, and an acidic catalyst, such a toluenesulfonic acid or ferric chloride, and ammonium chloride. As acid conditions are employed in forming the ketal protected carbonyl, it is possible that the nitrogen blocking group will be removed from the piperazine ring during the reaction, necessitating the reblocking of the nitrogen atom of the ketal-substituted derivative. A dialkyl hydrazone may be formed, for example by reaction of the ketone at the reflux temperature of an alcohol solvent with an unsymmetrical dialkyl hydrazine, such a dimethylhydrazine. Deprotection of the carbonyl moiety may take place prior to the coupling of the compounds of Formulas IIA and IV or, preferably, after coupling.

When X is unprotected carbonyl and $R_a$ is protected hydroxy, the protecting group must be removed from the polypeptide derivative of Formula I by means other than catalytic hydrogenation.

When X is hydroxymethylene, the dianion of Formula VII may be reacted with a benzoyl halide or ester of the above-defined structures, producing a ketone or protected ketone of Formula IIA, and the ketone or protected ketone coupled with a polypeptide of Formula IV, to yield a compound of Formula I wherein X is carbonyl, which is selectively reduced to yield a compound of Formula I wherein X is hydroxymethylene.

For example, the ketone of Formula I is dissolved in a solvent, such as acetic acid, ethyl acetate, or a lower aliphatic alcohol, such as methanol or isopropanol, and the solution agitated in the presence of hydrogen at from about 1 to about 4 atmospheres of pressure and room temperature, about 20° C. to 25° C., in the presence of a platinum or rhodium catalyst, and at least one equivalent of an acid until an equivalent of hydrogen gas is taken up, or is reacted for from about ½ to 8 hours at a temperature of from 0° C. to the reflux temperature of a lower aliphatic alcohol solvent, such as methanol or ethanol, with a metal borohydride, such as sodium borohydride or potassium borohydride.

Alternatively, when X is hydroxymethylene or when X and Z together form a methylidene radical, the dianion of Formula VII is reacted with a benzaldehyde of formula

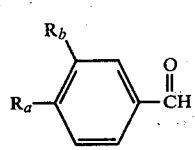

wherein $R_a$ and $R_b$ have the above-defined meanings. The resulting compound of Formula VIIIB wherein X" is hydroxymethylene or its alkoxide ion may be reacted for a period of about 1/5 to 16 hours, preferably for about ½ hour, with an acyl halide, such as acetyl chloride, to afford the dehydrated compound wherein X and Z are together methylidene or is reacted with a hydroxy protecting reagent to afford the protected derivative. For example, the carbinol of Formula VIIIB may be reacted in an ice bath with sodium hydride in dry THF, (2-methoxyethoxy)methyl chloride added and the mixture stirred at room temperature for from about ½ to about 3 hours to yield the (2-methoxyethoxy)methoxy derivative.

Benzaldehydes of the above-defined structure are commercially available or may be prepared by well-known methods from available compounds.

When X is thio, the dianion of Formula VII is reacted with a benzenesulfenyl halide of formula

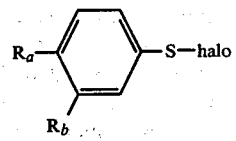

or a bis(benzene) disulfide of formula

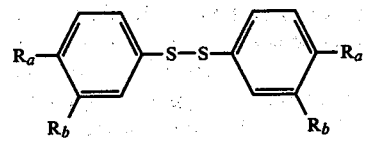

or a benzenesulfonothioic acid ester of formula

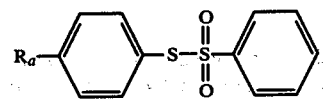

wherein $R_a$, $R_b$ and halo have the above-defined meanings, which are known compounds or may be prepared by methods well known in the art.

When X is sulfinyl, the dianion of Formula VII is reacted with a sulfinyl halide of formula

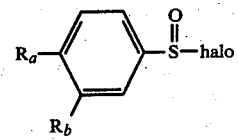

wherein $R_a$, $R_b$ and halo have the above-defined meanings, which are known compounds or may be prepared by methods well known in the art.

When X is sulfonyl, the dianion of Formula VII is reacted with a sulfonyl halide of formula

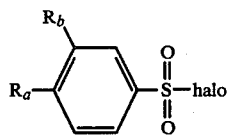

wherein $R_a$, $R_b$ and halo have the above-defined meanings, which likewise are known compounds or may be prepared by methods well known in the art.

When Z is straight chain lower alkyl, the order of the alkylation may be reversed, the dianion of Formula VII being reacted with an alkyl halide and the regenerated dianion being reacted with an electrophilic reagent of the above-defined type, to give a compound of Formula VIIIC, which is reacted with a base to give the monoanion and then with an α-haloacetic acid ester, as hereinabove described.

Alternatively, compounds of formula VIIIB or VIIIC wherein X is methylene may be prepared by reductive cyclization of the corresponding (N-benzyl-N-cyanomethyl)phenylalanine derivative according to the general method disclosed by R. Kunstmann, et al., in W. German Offen. No. 2,438,965, followed by debenzylation and protection of the ring nitrogen and of hydroxy substituents when they are present. Analogs of Formula VIIIB wherein X and Z form methylidene may alternatively be prepared by dehydrohalogenation of the corresponding 3-(α-halobenzyl)piperazinone, for example by the general method disclosed by H. Moureu et al., in Bull. Soc. Chim. France 1956, p.1785–7, followed by suitable protecting procedures. Compounds of Formula VIIIB and VIIIC so prepared may be alkylated by α-haloacetic acid esters in the above-described manner.

If desired, the individual enantiomers of the piperazinone derivatives may be separated at any stage following the introduction of the asymmetric carbon atom at C-3, by means of any suitable art-recognized means of resolution. For example, the piperazine nitrogen atom of an ester of Formula IIB may be deblocked and the resulting amine reacted with an optically active acid, for example L-tartaric acid, to give diasteriomeric salts, which may be separated by, for example, crystallization, and the individual enantiomers regenerated by treatment with aqueous base, extracted into a suitable solvent, such as methylene chloride, ethyl acetate, or benzene, and evaporated to dryness. The resolved ester is then reblocked to give the individual enantiomer of ester IIA.

Compounds of Formula IIIA are prepared according to general Reaction Scheme II:

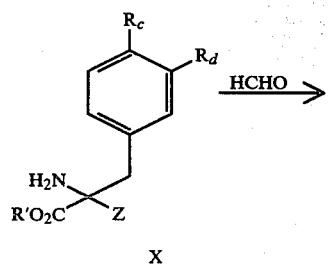

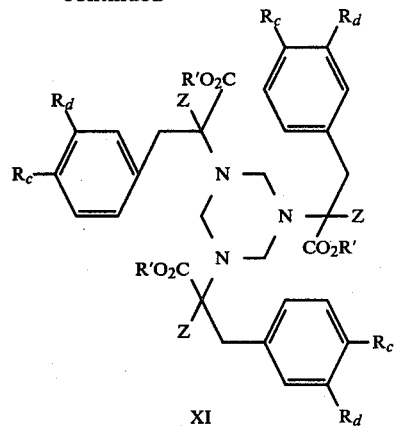

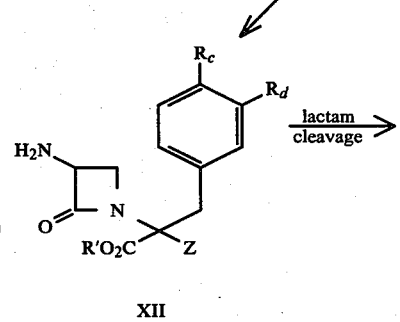

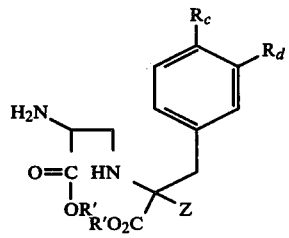

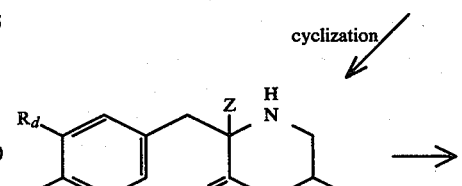

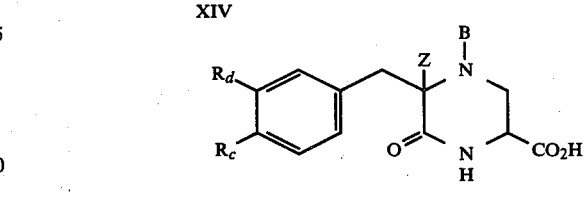

A phenylalanine derivative of Formula X wherein $R_c$ is hydrogen, halogen or benzyloxy and $R_d$ is hydrogen or $R_c$ and $R_d$ are both benzyloxy, Z is hydrogen or straight chain lower alkyl of from 1 to 5 carbon atoms, and R' is lower alkyl of from 1 to 4 carbon atoms or benzyl is reacted with an excess, for example 1½ to 3 equivalents, of formalin at a temperature of from about −20° C. to 25° C., preferably about 0° C., in the presence of a suitable organic solvent, for example, ethyl acetate, toluene or methylene chloride, for from about 1 to about 8 hours, preferably about 2 hours to yield a trimeric product, the 1,3,5-triazinetriacetate of Formula XI, which is isolated by standard methods, for example by extraction into an organic solvent and evaporation of the solvent.

Phenylalanine derivatives of Formula X are well known compounds, which are commercially available or may be prepared by well known methods, for example by the general procedure disclosed in Belgian Pat. No. 868,881. Preferably the L-enantiomer of the phenylalanine derivative is used in the preparation of the compounds of this invention.

The 1,3,5-triazinetriacetic acid derivative of Formula XI is cleaved by treatment with a Lewis acid and the resulting methyleneimine is subjected to a 2+2 cycloaddition reaction with an excess of an aminoacetyl reagent in the presence of a strong tertiary amine base, such as triethylamine of diazabicyclononane. The reaction is carried out under an inert atmosphere, for example under dry argon, for from 1 to 24 hours, preferably 2 to 3 hours, at a temperature of from −25° C. to −5° C. in the presence of an anhydrous halogenated solvent, for example methylene chloride or chloroform. The Lewis acid is preferably boron trifluoride etherate, but may also be, for example tin (IV) chloride, titanium (IV) chloride, aluminum chloride or other Lewis acids, and is employed in the molar ratio of 3 equivalents of Lewis acid per equivalent of 1,3,5-triazinetriacetate trimer.

Suitable aminoacetyl reagents include phthalimidoacetyl halides, mixed anhydrides of tertiary butoxycarbonylaminoacetic acid, and azidoacetyl halides. The preferred aminoacetyl reagent is phthalimidoacetyl chloride. In the preferred cycloaddition method, a solution of 1½ to 2 equivalents of phthalimidoacetyl chloride in dry methylene chloride is added dropwise to a stirred mixture of the trimer with 3 equivalents of $BF_3 \cdot Et_2O$ in dry methylene chloride under argon and, following this addition, a similar excess of triethylamine, which has been dried by storage over potassium hydroxide, is added dropwise, maintaining the temperature at −25° C. to −5° C., and the reaction allowed to continue for 2 to 3 hours at −20° C. to −5° C. The reaction is quenched and the resulting mixture of diastereomeric N-substituted β-lactams isolated by conventional methods, for example by extraction or chromatography, and the residue of the aminoacetyl cycloaddition reagent is cleaved or modified by an appropriate method to yield a 3-amino-β-lactam of general Formula XII.

Appropriate methods for removal of the residue of the phthaloyl and t-butoxycarbonyl groups and reduction of the azido group are well known. The azido group may, for example by reduced to yield a β-lactam of general Formula XII by catalytic hydrogenation in the presence of a platinum catalyst. When $R_c$ is benzyloxy, such hydrogenation may also serve to debenzylate the phenolic residue, necessitating the additional step of reprotecting the hydroxy substituent, $R_1$. When a t-butoxycarbonylaminoacetic acid mixed anhydride is employed as the cyclization reagent, the t-boc moiety may be removed by any of the known methods of deblocking t-boc protected amino groups, as described above. The phthaloyl moiety is cleaved by reaction of the phthaimido lactam with one equivalent of 3-(dimethylamino)propylamine or, preferably, hydrazine, in the presence of a suitable solvent, such as a primary alcohol of formula R'OH, wherein R' has the meaning defined above, at a temperature of from 0° C. to the boiling temperature of the solvent, preferably at about room temperature, or about 25° C., for from 4 to 48 hours, preferably about 24 hours.

The resulting β-lactams of general Formula XII are isolated, according to standard methods, for example by solution in an organic solvent, filtration and evaporation of the solvent, and dissolved in an alcohol solvent of formula R'OH. The solution is saturated with a strong acid, for example dry HCl, and the solution is permitted to stand at room temperature for from about 8 hours to about 4 days or is refluxed at the boiling temperature of the solvent for about 1 to 4 hours, until the cleavage of the β-lactam is complete, yielding the diastereomers of the diester of the general Formula XIII, which may be isolated, for example, by neutralization with an inorganic base, such as $NaHCO_3$ and extraction with an appropriate organic solvent, for example methylene chloride.

The diester of Formula XIII is cyclized by incubation in a protic solvent at pH 8.5–12, for from about 8 hours to 3 days, preferably about 1 day, at room temperature to yield the 6-oxo-2-piperazinecarboxylic acid ester of general Formula XIV. The solution may be made basic with a suitable base, such as alkali metal bicarbonates and carbonates, tertiary amines, such as triethylamine, and anionic exchange resins. Suitable solvents are protic solvents, such as alcohols of formula R'OH. The preferred base for cyclization of the diester of Formula XIII is an anion exchange resin adjusted, for example with sodium hydroxide, to pH 8.5–9. Suitable anion exchange resins are well known in the art and include, for example AG2-X8, a crosslinked polystyrene resin produced by Bio-Rad Laboratories Inc., and Dowex 2-X8, a similar resin produced by the Dow Chemical Co. Cyclization procedes spontaneously in the absence of added base in polar protic solvents, such as methanol, in about 3 days.

Following the cyclization, the compound of Formula XIV is isolated by standard procedures, the 4-position of the piperazine ring protected with a blocking reagent by standard methods, as described above, and the ester hydrolyzed, to yield a compound of Formula IIIA.

The procedure described above yields a mixture of diastereomeric 6-oxo-2-piperazinecarboxylic acid derivatives. When optically active forms of the phenylalanine derivative of Formula X are employed, crystallization or chromatography effects resolution of the two isomers generated by introduction of an additional asymmetric carbon atom. The individual diastereomers may be separated by standard methods at any convenient point in the synthetic process after the cycloaddition step. Preferably, the diastereomers of the protected precursor of the β-lactam of Formula XII are separated, using conventional methods, by fractional crystallization, column chromatography, or thin layer chromatography with a suitable solvent system. Alternatively, a compound of Formula IIIA or the blocked ester derived from Formula XIV, may similarly be separated into individual diastereomers by fractional crystallization or chromatography.

Compounds of general Formula IIIA and Formula XIV are also novel compounds and represent a part of this invention.

The preparation of the compounds of the present invention is further illustrated by the following examples. In the following description, ph means phenyl; $CO_2+$ or t-boc means tertiary-butoxy carbonyl; TFA means trifluoroacetic acid; and gly, phe and leu mean respectively residues of glycine, phenylalanine and leucine. Other abbreviations used herein have the well recognized standard chemical meaning.

Also, the number of the specific example corresponds to the compound number as assigned in the schematic chemical flow charts.

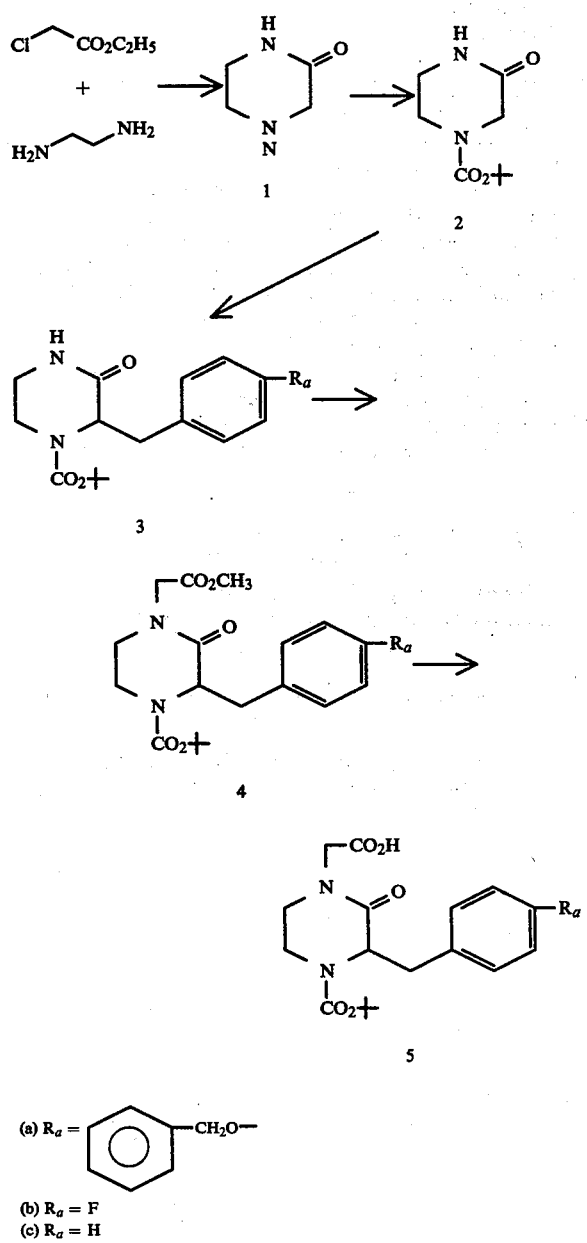

EXAMPLE 1

2-Piperazinone (1)

Prepared according to the procedure of S. R. Aspinall, *J. Amer. Chem. Soc.*, 62, 1202 (1940).

EXAMPLE 2 t-Butyl 3-Oxo-1-piperazinecarboxylate (2)

To a mixture of piperazinone 1 (1.0 g, $1.0 \times 10^{-2}$ mole) and sieve dried THF (15 ml) is added dropwise a solution of di-tert-butyl dicarbonate (2.4 g, $1.1 \times 10^{-2}$ mole) and sieve dried THF (5 ml). Evolution of $CO_2$ occurs immediately and the starting material slowly dissolves. After stirring at room temperature overnight the solvent is evaporated at reduced pressure affording 2 as a beige solid which crystallized from ethyl acetate/hexane as colorless plates: 1.2 g (60%), m.p. 159°–161° C.

EXAMPLE 3a t-Butyl 3-Oxo-2[4-benzyloxybenzyl]-1-piperazinecarboxylate (3a)

To a solution of dry diisopropylamine (7.7 ml, $5.5 \times 10^{-2}$ mole) and dry THF (25 ml) under argon at 0° C. is added dropwise a hexane solution of n-butyllithium (21.1 ml, $5.5 \times 10^{-2}$ mole). After stirring ½ hour at 0° C. a solution of t-boc-piperazinone (2) (5.0 g, $2.5 \times 10^{-2}$ mole) and dry THF (125 ml) is added dropwise. The resultant mixture is stirred at 0° C. for 3 hours before a solution of p-benzyloxybenzyl chloride (6.40 g, $2.75 \times 10^{-2}$ mole) and dry THF (20 ml) is added dropwise via syringe. This mixture is stirred an additional hour at 0° C. before the cooling bath is removed and the reaction allowed to warm to room temperature. After stirring overnight the mixture is quenched into saturated aqueous $NH_4Cl$. The aqueous phase is extracted with $Et_2O$ (3 times) and $CH_2Cl_2$ (2 times). The ethereal extracts are combined and subsequently washed with saturated aqueous NaCl as are the $CH_2Cl_2$ extracts. The ethereal and $CH_2Cl_2$ extracts are then combined and dried over $Na_2SO_4$. Filtration of the drying agent and evaporation of the filtrate gives 3a as an almost colorless solid which crystallizes from ethyl acetate as colorless prisms 5.2 g (53%), m.p. 145°–147° C.

EXAMPLE 3b t-Butyl 3-Oxo-2-(4-fluorobenzyl)-1-piperazinecarboxylate (3b)

When in the procedure of Example 3a, 4-fluorobenzyl chloride is substituted for p-benzyloxybenzyl chloride, the title compound is produced. M.p. 145°–147° C.

EXAMPLE 3c t-Butyl 3-Oxo-2-benzyl-1-piperazinecarboxylate (3c)

When in the procedure of Example 3a benzyl bromide is substituted for p-benzyloxybenzyl chloride, the title compound is produced. M.p. 152°–4° C.

EXAMPLE 4a

Methyl 4-(t-Butoxycarbonyl)-2-oxo-3-(4-benzyloxybenzyl)-1-piperazineacetate (4a)

To a solution of t-boc-(4-benzyloxybenzyl)piperazinone 3a (2.66 g, $6.72 \times 10^{-3}$ mole) and dry THF (20 ml) under argon at room temperature is added portionwise NaH (0.30 g, $7.4 \times 10^{-3}$ mole, 59% oil dispersion). After stirring ½ hour at room temperature a solution of methyl α-bromoacetate (0.62 ml, $7.4 \times 10^{-3}$ mole) is added via syringe. After stirring overnight the reaction mixture is poured into water which is subsequently extracted with Et₂O (3 times). The combined ethereal extracts are washed with saturated aqueous NaCl before being dried over Na₂SO₄. Filtration of the drying agent and evaporation of the filtrate affords a viscous oil which after column chromatography (silica gel, 10% EtOAc/CHCl₃) gives a clear, colorless oil. After standing in the refrigerator this oil crystallizes. The resulting solid is triturated with hexane and collected by filtration affording 4a as colorless matted needles: 2.3 g (74%), m.p. 84°–87° C.

EXAMPLE 4b

Methyl 4-(t-Butoxycarbonyl)-2-oxo-3-(4-fluorobenzyl)-1-piperazine acetate (4b)

When in the procedure of Example 4a, 3b is substituted for 3a, the title compound is produced.

EXAMPLE 4c

Methyl 4-(t-Butoxycarbonyl)-2-oxo-3-benzyl-1-piperazineacetate (4c)

When in the procedure of Example 4a, 3c is substituted for 3a, the title compound is produced.

EXAMPLE 4'a

Methyl 4-(t-Butoxycarbonyl)-2-oxo-3-(4-benzyloxybenzyl)-1-piperazineacetate (4a)

To a solution of dry diisopropylamine (0.31 ml, 2.2 mmole) in 2 ml of dry THF at 0° C. under argon was added dropwise via syringe a hexane solution of n-butyllithium (0.9 ml, 2.2 mmole). After about ½ hour, a solution of t-boc piperazinone (2) (0.200 g, 1.00 mmole) in 5 ml of THF was added dropwise via syringe. The resulting solution was allowed to metallate at 0° C. for 3 hours after which a solution of 4-benzyloxybenzyl chloride (0.256 g, 1.1 mmole) in 2 ml of dry THF was added and the resulting solution stirred at 0° C. for one hour, allowed to warm to room temperature and stirred overnight.

Methyl α-bromoacetate (0.095 ml, 1.1 mmole) was added to the solution via syringe and the solution stirred overnight at room temperature and quenched into ethyl ether/water. The aqueous phase was extracted twice with ether and the combined ethereal extracts washed with saturated sodium chloride solution and dried over Na₂SO₄. The solvent was evaporated and the resulting yellow oil chromatographed with 20% ethylacetate/chloroform to yield 4a, as an oil, which crystallized upon standing. M.p. 84°–87° C.

EXAMPLE 5a 4-(t-Butoxycarbonyl)-2-oxo-3-(4-benzyloxybenzyl)-1-piperazineacetic acid (5a)

t-Boc-piperazinoneacetate 4a (0.251 g, 5.37×10⁻⁴ mole), 1M aqueous LiOH (0.59 ml, 5.9×10⁻⁴ mole), and methanol (2 ml) are stirred at room temperature for 2 hours. The solvent is then evaporated and the resulting yellow oil is dissolved in CH₂Cl₂ and transferred to a separatory funnel where it is washed with 0.5M aqueous HCl. The CH₂Cl₂ layer is separated and the acidic aqueous phase is extracted with CH₂Cl₂ (3 times). The CH₂Cl₂ extracts are combined and washed with saturated aqueous NaCl before being dried over Na₂SO₄. Filtration of the drying agent and evaporation of the filtrate gives 5a as a colorless foam, which was shown to be homogeneous by TLC on silica gel plates. The structure of 5a was corroborated by NMR. NMR (CDCl₃) δ 1.27 (S, 9, t-boc), 3.09–4.07 (m, 8, methylenes), 4.68 (t, 1, C₃-H), 4.97 (S, 2, benzyloxy methylene), 6.89 (q, 4, aromatic), 7.30 (S, 5, aromatic), 9.99 (broad S, 1, acid).

The two enantiomers of 5 are separated via salt formation with d-(+)-α-methylbenzylamine and subsequent crystallization by procedures known in the art.

EXAMPLE 5b 4-(t-Butoxycarbonyl)-2-oxo-3-(4-fluorobenzyl)-1-piperazineacetic acid (5b)

When in the procedure of Example 5a, 4b is substituted for 4a, the title compound is produced.

EXAMPLE 5c 4-(t-Butoxycarbonyl)-2-oxo-3-benzyl-1-piperazineacetic acid (5c)

When in the procedure of Example 5a, 4c is substituted for 4a, the title compound is produced.

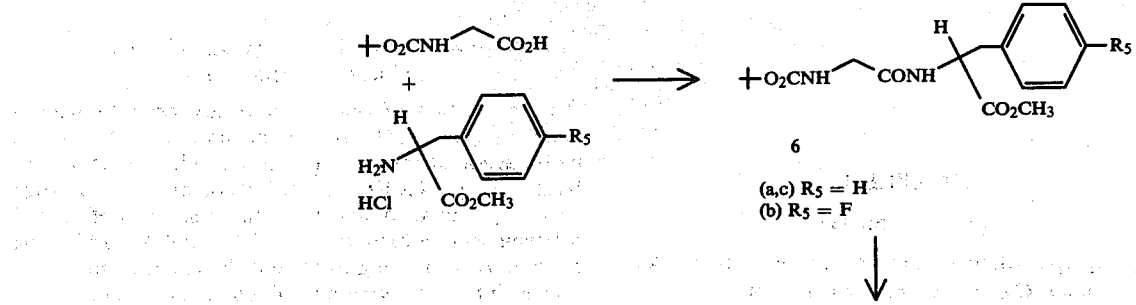

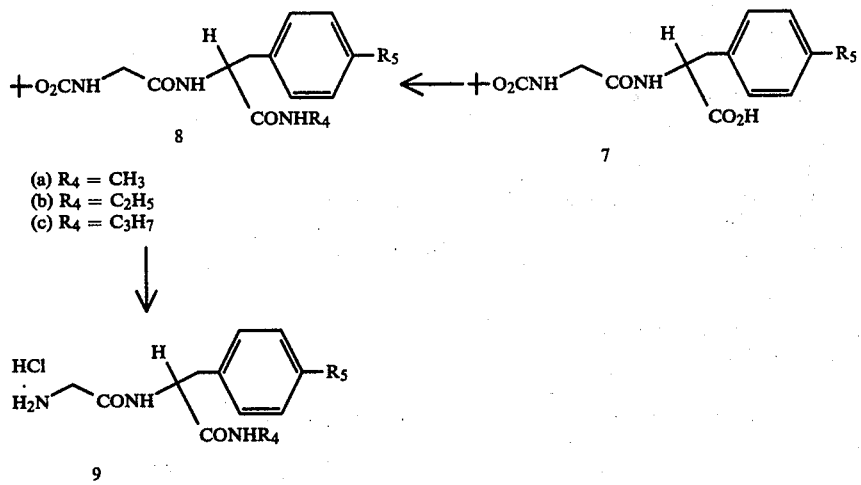

(a) R₄ = CH₃
(b) R₄ = C₂H₅
(c) R₄ = C₃H₇

EXAMPLE 6a

N-[N-(t-Butoxycarbonyl)glycyl]-L-phenylalanine methyl ester (6a)

t-Boc-glycine (1.75 g, 1.00×10⁻² mole), L-phenylalanine methyl ester hydrochloride (2.16 g, 1.00×10⁻² mole), and N-ethoxycarbonyl-2-ethoxy-1,2-dihydroquinoline (2.47 g, 1.00×10⁻² mole), and CH₂Cl₂ (50 ml) are stirred at room temperature for 16 hours. The reaction mixture is then washed in turn with 0.5M aqueous HCl (2 times) and saturated aqueous NaHCO₃ before being dried over Na₂SO₄. Filtration of the drying agent and evaporation of the filtrate gives 6a as an extremely viscous, almost colorless oil, which was shown to be homogeneous by TLC on silica gel plates and the structure corroborated by NMR. NMR (CDCl₃) δ 1.42 (S, 9, t-boc), 3.02 (d,2, benzylic methylene), 3.59 (S, 3, ester), 7.13 (S, 5, aromatic).

EXAMPLE 6b

N-[N-(t-Butoxycarbonyl)glycyl]-4-fluorophenylalanine methyl ester (6b)

1.8 g (10 mmole) of 4-fluorophenylalanine is suspended in 3.0 ml of methanol and cooled to −10° C. under nitrogen and 0.81 ml of thionylchloride added dropwise, keeping the temperature at or below −2° C., and stirred for 1 hour at −5° C. to −10° C. About 10 ml of methanol was added and the solution stirred at room temperature overnight. The solution was concentrated in vacuo and the residue triturated with dry ether and filtered to give the hydrochloride salt of 4-fluorophenylalanine methyl ester, m.p. 177.5° to 178° C. The ester hydrochloride is substituted for L-phenylalanine methyl ester hydrochloride in the procedure of Example 6a to yield 6b.

EXAMPLE 7a

N-[N-(t-Butoxycarbonyl)glycyl]-L-phenylalanine (7a)

t-Boc-gly-phe-OCH₃, 6a (9.2 g, 2.7×10⁻² mole), 1M aqueous LiOH (30 ml, 3.0×10⁻² mole), and methanol (100 ml) are stirred at room temperature for 2 hours. Most of the methanol is evaporated. The concentrate is diluted with water (10 ml) and transferred to a separatory funnel. The mixture is then acidified with 1M aqueous HCl (50 ml) and the aqueous acidic mixture subsequently extracted with CHCl₃ (4 times). The combined CHCl₃ extracts are washed with saturated aqueous NaCl before being dried over Na₂SO₄. Filtration of the drying agent and evaporation of the filtrate gives a foam which when triturated with Et₂O/hexane affords 7a as a colorless solid which crystallizes from ethyl acetate/hexane as colorless needles: 6.3 g (71%), m.p. 138°-141° C.

EXAMPLE 7b

N-[N-(t-Butoxycarbonyl)glycyl]-4-fluorophenylalanine (7b)

When in the procedure of Example 7a, 6b is substituted for 6a, the title compound is produced.

EXAMPLE 8a

Nα-[N-(t-Butoxycarbonyl)glycyl]-N-methyl-L-phenylalaninamide (8a)

To a solution of t-boc-gly-phe 7a (5.3 g, 1.6×10⁻² mole) in dry THF (80 ml) under argon at −10° C. is added in turn Et₃N (2.5 ml, 1.8×10⁻² mole) and isobutyl chloroformate (2.4 ml, 1.8×10⁻² mole). The resulting mixture is stirred at −10° C. for 10 minutes before a freshly neutrallized mixture of methylamine hydrochloride (3.3 g, 4.9×10⁻² mole), Et₃N (6.9 ml, 4.9×10⁻² mole), THF (80 ml), and H₂O (40 ml) is added in one portion. The cooling bath is then removed and the mixture allowed to warm to room temperature. After stirring overnight the reaction is quenched into saturated aqueous NaHCO₃. The aqueous alkaline mixture is extracted with Et₂O (3 times) and CH₂Cl₂ (2 times). The ethereal extracts are combined and subsequently washed with saturated aqueous NaCl as are the CH₂Cl₂ extracts. The ethereal and CH₂Cl₂ extracts are then combined and dried over Na₂SO₄. Filtration of the drying agent and evaporation of the filtrate gives a yellowish foam which when triturated with Et₂O affords 8a as a colorless solid which crystallizes from aqueous ethanol as colorless matted needles, 4.1 g (74%), m.p. 158°-160° C. In a similar fashion, t-boc-gly-phe-leu-NHEt is prepared from 7a and leucine ethylamide.

EXAMPLE 8b

N$^\alpha$-[N-(t-Butoxycarbonyl)glycyl]-N-ethyl-4-fluorophenylalaninamide (8b)

To 12 g of cooled liquid ethylamine in a small pressure bottle is added 2.8 g of t-boc-gly-4-F-phe OCH$_3$, 6b, and the solution stirred overnight at room temperature. Evaporation of the solvent gives a solid, which when recrystallized from 95% ethanol yields 8b, m.p. 181°–182.5° C. Alternatively, 8b may be prepared from 7b, according to the procedure of Example 8a.

EXAMPLE 8c

N$^\alpha$-[N-(t-Butoxycarbonyl)glycyl]-N-(n-propyl)-L-phenylalaninamide (8c)

When in the procedure of Example 8b, 6a is substituted for 6b and n-propylamine substituted for ethylamine, the produce is 8c, which recrystallizes from ethyl acetate/cyclohexane/methanol as a white solid. M.p. 166°–167.5° C.

EXAMPLE 9a

N$^\alpha$-Glycyl-N-methyl-L-phenylalaninamide hydrochloride (9a)

Gaseous HCl is bubbled through a solution of t-boc-gly-phe-NHCH$_3$ 8a (9.2 g, 2.7×10$^{-2}$ mole) and methanol (200 ml). After ½ hour the methanol is evaporated at reduced pressure leaving a clear colorless oil which, when triturated with Et$_2$O crystallizes to give 9a as a colorless power: m.p. 220°–223° C. In a similar fashion, gly-phe-leu-NHEt.HCl is prepared from its corresponding t-boc-derivative.

EXAMPLE 9b

N$^\alpha$-Glycyl-N-ethyl-4-fluorophenylalaninamide hydrochloride (9b)

When in the procedure of Example 9a, 8b is substituted for 8a, the product, which is recrystallized from absolute ethanol, is 9b. M.p. 251°–252° C.

EXAMPLE 9c

N$^\alpha$-Glycyl-N-propyl-L-phenylalaninamide hydrochloride (9c)

When in the procedure of Example 9a, 8c is substituted for 8a, the title compound is produced

5 + 9 ⟶

(a) R$_a$ = benzloxy,
   R$_5$ = H, x = 1
(b) R$_a$ = R$_5$ = F,
   x = 2

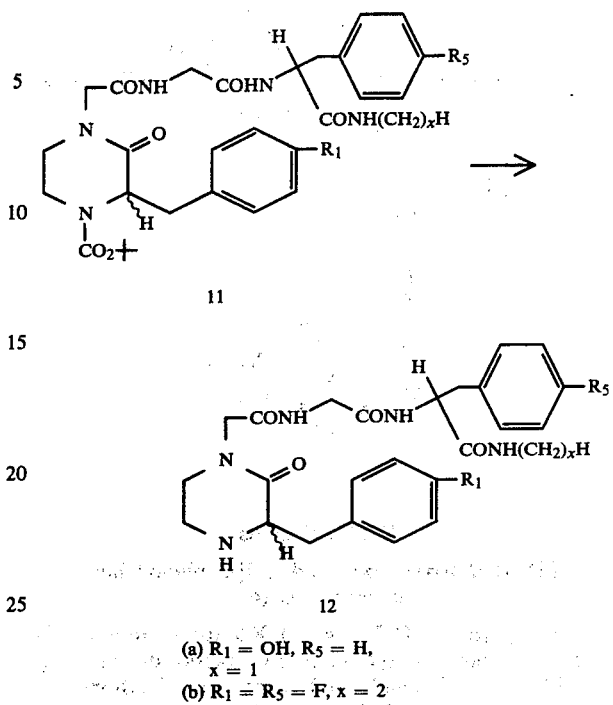

(a) R$_1$ = OH, R$_5$ = H,
   x = 1
(b) R$_1$ = R$_5$ = F, x = 2

EXAMPLE 10a

N$^\alpha$-[N-[[4-(t-Butoxycarbonyl)-2-oxo-3-(4-benzyloxybenzyl)-1-piperazinyl]acetyl]glycyl]-N-methyl-L-phenylalaninamide (10a)

To a solution of piperazinone acetic acid 5a (0.45 g, 1.0×10$^{-3}$ mole) and dry THF (3 ml) at −10° C. under argon is added in turn Et$_3$N (0.16 ml, 1.1×10$^{-3}$ mole) and isobutylchloroformate (0.15 ml, 1.1×10$^{-3}$ mole). After stirring 10 minutes at −10° C., a freshly neutralized solution of glycyl-L-phenylalanine methyl amide 9a hydrochloride (0.30 g, 1.1×10$^{-3}$ mole), Et$_3$N (0.28 ml, 2.0×10$^{-3}$ mole), THF (3 ml), and H$_2$O (1.5 ml) is added in one portion. The cooling bath is then removed and the reaction allowed to warm to room temperature. After stirring overnight the reaction is quenched into 0.5M aqueous HCl. The aqueous mixture is extracted with Et$_2$O (2 times) and CH$_2$Cl$_2$ (2 times). The ethereal extracts are combined and washed with saturated aqueous NaHCO$_3$ as are the CH$_2$Cl$_2$ extracts. The ethereal and CH$_2$Cl$_2$ extracts are then combined and dried over Na$_2$SO$_4$. Filtration of the drying agent and evaporation of the filtrate give 10a which is purified by chromatography, and the structure corroborated by NMR. NMR (CDCl$_3$) δ 1.26 (S, 9, t-boc), 2.64 (d, 3, methylamide), 3.08, 3.90 (m, 12, methylenes), 4.68 (m, 2, C$_3$-H and phenylala —CH), 4.98 (S, 2, benzyloxy methylene), 6.6–7.8 (m, 17, aromatic and amide NH's).

EXAMPLE 10b

N$^\alpha$-[N-[[4-(t-Butoxycarbonyl)-2-oxo-3-(4-fluorobenzyl)-1-piperazinyl]acetyl]glycyl]-N-ethyl-4-fluorophenylalaninamide (10b)

When in the procedure of Example 10a, 5b is substituted for 5a and 9b is substituted for 9a, the title compound is produced.

EXAMPLE 11

N$^\alpha$-[N-[[4-(t-Butoxycarbonyl)-3-(4-hydroxybenzyl)-2-oxo-1-piperazinyl]acetyl]glycyl]-N-methyl-L-phenylalaninamide (11a)

Protected-piperazinoneacetyl-gly-phe-NHCH$_3$, 10a, (6.71 g, 1.00×10$^{-2}$ mole) in ethanol (100 ml) is hydrogenated in a Parr apparatus at 40 psi over 10% Pd/C (0.5 g). After the reaction has absorbed one equivalent of hydrogen, the catalyst is filtered and washed with ethanol. The filtrate is evaporated at reduced pressure, affording 11a.

EXAMPLE 12a

N$^\alpha$-[N-[[3-(4-Hydroxybenzyl)-2-oxo-1-piperazinyl]acetyl]glycyl]-N-methyl-L-phenylalaninamide (12a)

Piperazinone acetyl-gly-phe-NHCH$_3$ 11a (0.58 g, 1.0×10$^{-3}$ mole) and trifluoroacetic acid are stirred at room temperature for ½ hour. The solvent is then evaporated and the residue dissolved in CH$_2$Cl$_2$. The CH$_2$Cl$_2$ solution is washed in turn with saturated aqueous NaHCO$_3$ and saturated aqueous NaCl before being dried over Na$_2$SO$_4$. Filtration of the drying agent and evaporation of the filtrate give 12a which is purified by chromatography and the structure corroborated by NMR. NMR (Acetone-d$_6$) δ (d, 3, methyl amide), 3.0–4.3 (m, 14, methylenes and phenolic-OH), 4.53 (m, 1, phenylalanine methine), 6.88 (8, 4, aromatic), 7.25 (s, 5, aromatic), 7.6–8.0 (m, 3, amide NH's).

In a similar sequence of reactions, 3-(4-hydroxybenzyl)-2-piperazinoneacetyl-gly-phe-leu-NHEt is prepared from 5a and gly-phe-leu-NHEt.HCl.

EXAMPLE 12b

N$^\alpha$-[N[[3-(4-Fluorobenzyl)-2-oxo-1-piperazinyl]acetyl]glycyl]-N-ethyl-4-fluorophenylalaninamide (12b)

When in the procedure of Example 12a, 10b, is substituted for 11a, the title compound is produced.

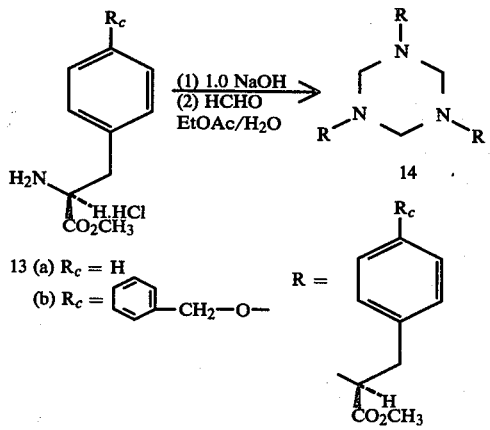

13 (a) R$_c$ = H
(b) R$_c$ = <phenyl>—CH$_2$—O—

R = <image inline: 4-R$_c$-phenyl-CH$_2$-CH(CO$_2$CH$_3$)-H>

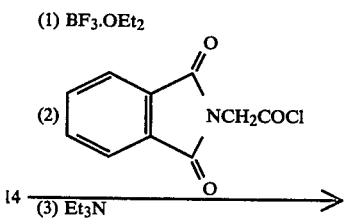

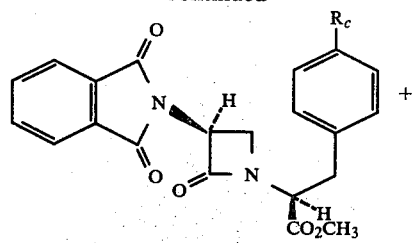

15 (syn) (a) R$_c$ = H
(b) R$_c$ = <phenyl>—CH$_2$O—

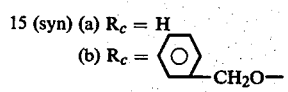

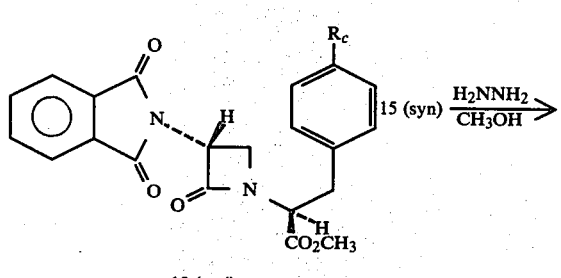

15 (anti)

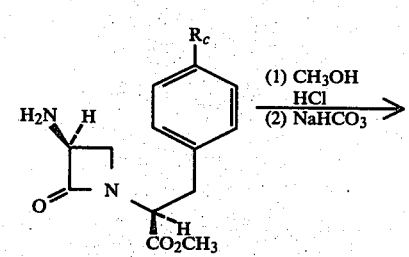

16 (syn)

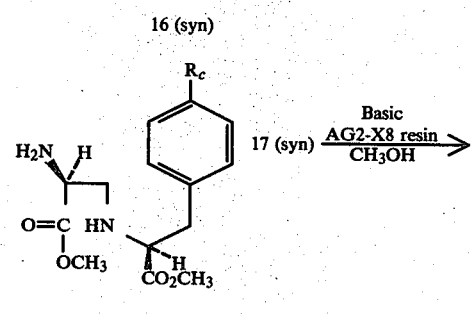

17 (syn)

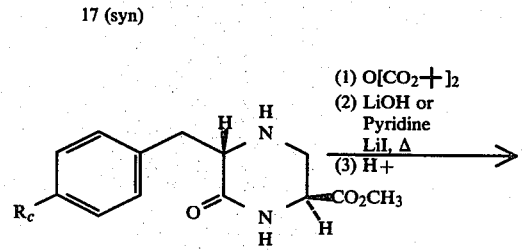

18 (trans)

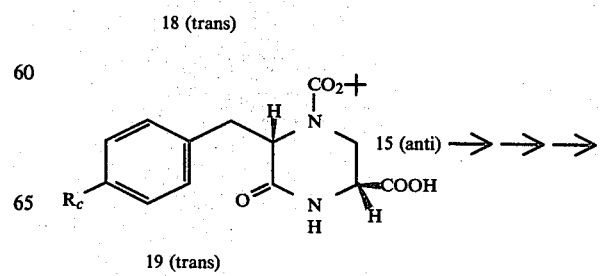

19 (trans)

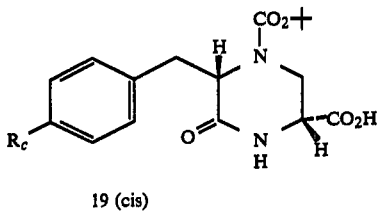

19 (cis)

EXAMPLE 13

The compounds represented as 13 are commercially available.

EXAMPLE 14a

Trimethyl α,α′,α″-Tribenzyl-1,3,5(2H,4H,6H)-triazine-1,3,5-triacetate (14a)

10.0 g (46.4 mmole) of L-phenylalanine methyl ester hydrochloride 13a was dissolved in 60 ml H$_2$O and cooled to 0° C. 1.90 g (47.5 mmole) of NaOH pellets were added with vigorous stirring. After solution was complete, 30 ml of ethyl acetate was added, followed by dropwise addition of 7.6 ml (100 mmole) of 37% formalin solution. The mixture was stirred at 0° C. for 2 hours, then poured into dilute aqueous NaCl and extracted twice with ethyl acetate. The extracts were washed with brine, dried over Na$_2$SO$_4$, and concentrated in vacuo to give 8.3 g of semi-crystalline material. Recrystallization from cyclohexane/EtOAc gave 7.95 g (89.7%) of white needles 14a: M.p. 134°–137.5° C.; $[\alpha]_D^{25} = -101.1$ (C=4.37, EtOAc).

Substituting DL-phenylalanine methyl ester HCl for L-phenylalanine methyl ester HCl, one obtains the DL analog of 14a which is recrystallized from cyclohexane to give white crystals: M.p. 106°–108.2° C.

EXAMPLE 14b

Trimethyl α,α′,α″-Tris (4-benzyloxybenzyl)-1,3,5-(2H,4H,6H)triazine-1,3,5-triacetate (14b)

Substituting O-benzyl-L-tyrosine methyl ester hydrochloride for L-phenylalanine methyl ester hydrochloride in Example 14a, one obtains 14b in 96% yield as a yellow oil which partially crystallizes on standing. NMR (CDCl$_3$) δ 7.4–6.6 (m, 9H), 4.87 (s, 2H), 3.8–3.3 (m, 6H, —OCH$_3$ at 3.53), 2.78 (d, J=7 Hz, 2H).

EXAMPLE 15a

Methyl 3-Phthalimido-2-oxo-α-benzyl-1-azetidineacetate (15a)

To a stirred solution of 21.4 g (37.3 mmole) of 14a in 750 ml dry CH$_2$Cl$_2$ (freshly distilled from P$_2$O$_5$) under Ar is added 13.8 ml (112 mmole) of BF$_3$.OEt$_2$ distilled from CaH$_2$. The solution is stirred 20 minutes at 25° C., before being cooled to −25° C. to −20° C. A solution of 30.1 g (135 mmole) of phthalimidoacetyl chloride in 70 ml dry CH$_2$Cl$_2$ is added dropwise over 20 minutes. Thirty-five (35) minutes after the completion of the addition of acid chloride, 34.3 ml (247 mmole) of Et$_3$N, dried by storing over KOH pellets, is added dropwise over 10 minutes while keeping the solution at −25° C. to −20° C. A bright orange color appears but rapidly dissipates upon addition of each drop of Et$_3$N in the early stages of the addition; the orange color persists near the end of the addition. The reaction mixture is maintained at −25° C. to −5° C. for 2¼ hours, then poured into ice water and extracted twice with CH$_2$Cl$_2$/EtOAc/ether. The extracts are washed twice with cold 5% HCl, once with H$_2$O, twice with aqueous NaHCO$_3$, and with brine and dried over Na$_2$SO$_4$. Concentration in vacuo gives a semi-crystalline orange oil which is suspended in ethyl acetate and filtered. The filtrate is concentrated and recrystallized from 175 ml of CH$_3$OH/EtOA to give 12.8 g (30.3%) of pure 15a (syn) as white needles. A second recrystallization gives analytically pure 15a (syn): m.p. 153°–155.5° C.; $[\alpha]_D^{25} = -135.7$ (C=2.4958, EtOAc).

The mother liquid is chromatographed on 650 g of silica gel eluting with 1.68% CH$_3$OH/CH$_2$Cl$_2$, to give 18.9 g of a mixture of (syn) and (anti) 15a, which was predominately 15a (anti), as a yellow oil, and an unidentified third product [β-lactams 15a (syn and anti) constitute about ⅔ of the mixture].

The purified mixture of β-lactams 15a (syn and anti) prepared from DL-phenylalanine methyl ester exhibited the following spectral characteristics: IR (neat) 1765, 1740, 1720 cm$^{-1}$; NMR (CDCl$_3$) δ 7.90–7.58 (m, 4H). 7.24 and 7.22 (2s, 5H), 5.40 (dd, J=4, 5 Hz) 5.22 (dd, J=3.5, 6 Hz) 4.93–4.10 (m, 2H total for all signals δ 5.4–4.10), 3.95–3.53 (m, 1H), 3.79 and 3.67 (2s, 3H), 3.35–3.05 (m, 2H).

EXAMPLE 15b

Methyl 3-Phthalimido-2-oxo-α-(4-benzyloxybenzyl)-1-azetidine-acetate (15b)

Substituting 14b for 14a in Example 15a, one obtains after chromatography of the crude reaction mixture 15b in 34–43% yield as off-white semi-crystalline material, which is recrystallized from CH$_3$OH/EtOAc to yield white crystalline 15b (syn): m.p. 147°–148.5° C., $[\alpha]_D^{25} = -105.3$ (c=2.039, EtOAc). The mother liquid is concentrated to give a yellow oil which is a mixture of (syn) and (anti) 15b, which was predominately 15b (anti).

The purified mixture of β-lactams 15b (syn and anti) exhibited the following spectral characteristics: IR (neat) 1770, 1745, 1720 cm$^{-1}$; NMR (CDCl$_3$) δ 7.68 (bs, 4H), 7.33 (s, 5H) 7.08–6.80 (m, 4H), 5.38–5.13 (m, 1H), 5.00 (s, 2H), 4.9–4.61 (m, 1H), 3.96–3.38 (m, 4H, —OCH$_3$ at 3.78 and 3.68), 3.33–2.95 (m, 2H).

EXAMPLE 16

Methyl 3-Amino-2-oxo-α-benzyl-1-azetidineacetate (16a (syn))

To a stirred suspension of 6.42 g (17.0 mmole) of 15a (syn) in 75 ml of dry methanol under argon is added dropwise via syringe 0.600 ml (18.3 mmole) of 97% anhydrous hydrazine. The solution is stirred at 25° C. for 21 hours and then concentrated in vacuo. CH$_2$Cl$_2$ is added, and the mixture filtered through celite to remove phthalhydrazide. The filtrate is concentrated to give 4.7 g of 16a as a clear colorless oil. NMR (CDCl$_3$) δ 7.20 (s, 5H), 4.63 (dd, J=6, 9 Hz, 1H), 3.90 (dd, J=2.5, 5.5 Hz, 1H), 3.70 (s, 3H), 3.55–3.3 (m, ~2H), 3.2–2.8 (m, ~2H), 2.5–1.8 (bs, 2H).

EXAMPLE 17

N-[2-Amino-2(methoxycarbonylethyl)]-L-phenylalanine methyl ester dihydrochloride (17a (syn))

The 16a (syn) produced in Example 16 is dissolved in 150 ml of dry methanol, the solution saturated with HCl gas, becoming very hot during saturation, and the solution allowed to stand at room temperature for 1 day. The solution is concentrated in vacuo, 200 ml of water is added and the mixture filtered and washed with ethyl acetate. The filtrate is made basic with $NaHCO_3$ and extracted twice with $CH_2Cl_2$. The combined extracts were dried ($Na_2SO_4$) and concentrated in vacuo to give 4.5 g of 17a (syn) as a colorless oil. NMR ($CDCl_3$) δ 7.20 (s, 5H), 3.73–3.3 (m, 8H, —$OCH_3$ and 3.65 and 3.62), 3.03–2.66 (m, 4H), 1.73 (bs, 3H).

EXAMPLE 18a trans-Methyl 6-oxo-5-benzyl-2-piperazinecarboxylate (18a (trans))

The oil produced in Example 17 is dissolved in 200 ml of methanol and 4.5 g of AG2-X8 anion exchange resin, made basic by washing with 2N NaOH, with water until the filtrate was neutral, and finally with methanol, added and the mixture is stirred at room temperature for 10 minutes, then filtered, washing the resin with 2×25 ml of methanol. The filtrate is allowed to stand at room temperature for 18 hours, then concentrated in vacuo to give 3.97 g [94% overall from 15a (syn)] of 18a (trans) as colorless crystals. Recrystallization from cyclohexane/EtOAc gives white crystals. M.p. 101.5°–103.5° C. NMR ($CDCl_3$) δ 7.21 (s, 5H) 6.26 (bs, 1H), 4.09 (dd, J=4.5, 10 Hz, 1H), 3.72 (s, 3H), 3.66–3.26 (m, 3H), 3.00–2.69 (m, 2H), 1.64 (s, 1H).

cis-Methyl 6-oxo-5-benzyl-2-piperazinecarboxylate (18a (cis))

When 15a (anti) is substituted for 15a (syn) in the procedure of Example 16 and the product reacted according to the procedures of Example 17 and in the manner described above, 18a (cis) is obtained as a pale yellow viscous oil.

EXAMPLE 18b trans-Methyl 6-oxo-5-(4-benzyloxybenzyl)-2-piperazinecarboxylate (18b (trans))

When 15b (syn) is substituted for 15a (syn) in the procedure of Example 16 and the product reacted according to the procedures of Example 17 and 18a, 18b (trans) is obtained as white crystals. M.P. 126°–128° C.

cis-Methyl 6-oxo-5-(4-benzyloxybenzyl)-2-piperazinecarboxylate (18b (cis)) hydrochloride When 15b (anti) is substituted for 15a (syn) in the procedure of Example 16 and the product reacted according to the procedures of Examples 17 and 18a, 18b (cis) is obtained as an oil, which was stirred in ethanolic HCl and the resulting HCl salt recrystallized from butanone/methanol. M.p. 207°–209° C. (dec.).

EXAMPLE 19a trans-5-Oxo-6-benzyl-1,3-piperazinedicarboxylic acid 1-t-butyl ester (19a (trans))

A mixture of 7.40 g (29.8 mmole) of crude 18a (cis and trans) and 7.6 ml (33 mmole) of di-tert-butyl dicarbonate in 75 ml of tetrahydrofuran was heated at 50°–55° C. for 2 hours. The solution was concentrated in vacuo and chromatographed on 300 g of silica gel with 2.8% $CH_3OH/CH_2Cl_2$ to obtain 3.2 g of t-Boc-substituted 18a (cis) and 1.6 g of t-Boc'ed 18a (trans). Recrystallization of each from $CH_2Cl_2$/cyclohexane gives t-Boc'ed 18a (cis), m.p. 152°–155.5° C., and t-Boc'ed 18a (trans), m.p. 174°–176° C., each as fine white crystals.

A solution of 1.15 g (3.30 mmole) of t-Boc'ed 18a (trans) and 1.32 g (9.90 mmole) of LiI in 10 ml of pyridine was heated at reflux under argon for 3 hours. The solution was cooled and concentrated in vacuo. The oil was dissolved in water and washed twice with ether. The aqueous layer was then acidified with cold dilute aqueous HCl and extracted with EtOAc/$CH_2Cl_2$. The extract was washed with $H_2O$ and brine and dried ($Na_2SO_4$). Concentration in vacuo gave 0.77 g (70%) of off-white solid. Recrystallization from EtOAc/$CH_3OH$ gives pure 19a (trans). M.p. 193°–194° C. (dec.).

Cis 5-Oxo-6-benzyl-1,3-piperazinedicarboxylic acid 1-t-butyl ester (19a (cis))

To a solution of 0.25 g (0.72 mmole) of t-Boc'ed 18a (cis) in 10 ml of methanol was added 1.2 ml of 1.0M LiOH and the resulting solution allowed to stir at 25° C. for 18 hours. The solution is concentrated in vacuo and the residue partitioned between water and ether. The aqueous layer is acidified with cold dilute aqueous HCl and extracted with ether. The extract is dried ($MgSO_4$) and concentrated in vacuo to give 0.16 g (67%) of 19a (cis) as white crystals. Recrystallization from EtOAc/$CH_3OH$ gives pure 19a (cis). NMR ($CDCl_3$) δ 7.73 (bs, 1H), 7.5 (bs, 1H), 7.22 (s, 5H), 4.83–3.93 (m, 3H), 3.27–2.5 (m, 3H), 1.25 (s, 9H).

EXAMPLE 19b

Cis 5-Oxo-6-(4-benzyloxybenzyl)-1,3-piperazinedicarboxylic acid, 1-t-butyl ester (19b (cis))

When in the procedure of Example 19a, 18b (cis) is substituted for 18a (trans), the crude t-Boc derivative of 18b (cis) is obtained. NMR ($CDCl_3$) δ 7.3 (s), 7.15–6.73 (m), 4.96 (s), 4.8–3.9 (m), 3.71 (s), 3.2–2.65 (m), 1.25 (s). Subsequent hydrolysis gives the title compound.

trans 5-Oxo-6-(4-benzyloxybenzyl)-1,3-piperazinedicarboxylic acid, 1-t-butyl ester (19b (trans))

When in the procedure of Example 19a, 18b (trans) is substituted for 18a (trans), the t-Boc derivative of 18b (trans) is obtained. NMR ($CDCl_3$) δ 7.55 (m, 1H), 7.33 (s, 5H), 7.13–6.75 (m, 4H), 5.00 (s, 2H), 4.83–3.77 (m, 3H), 3.70 (s, 3H), 3.25–2.6 (m, 3H), 1.28 (s, 9H). Subsequent hydrolysis gives the title compound.

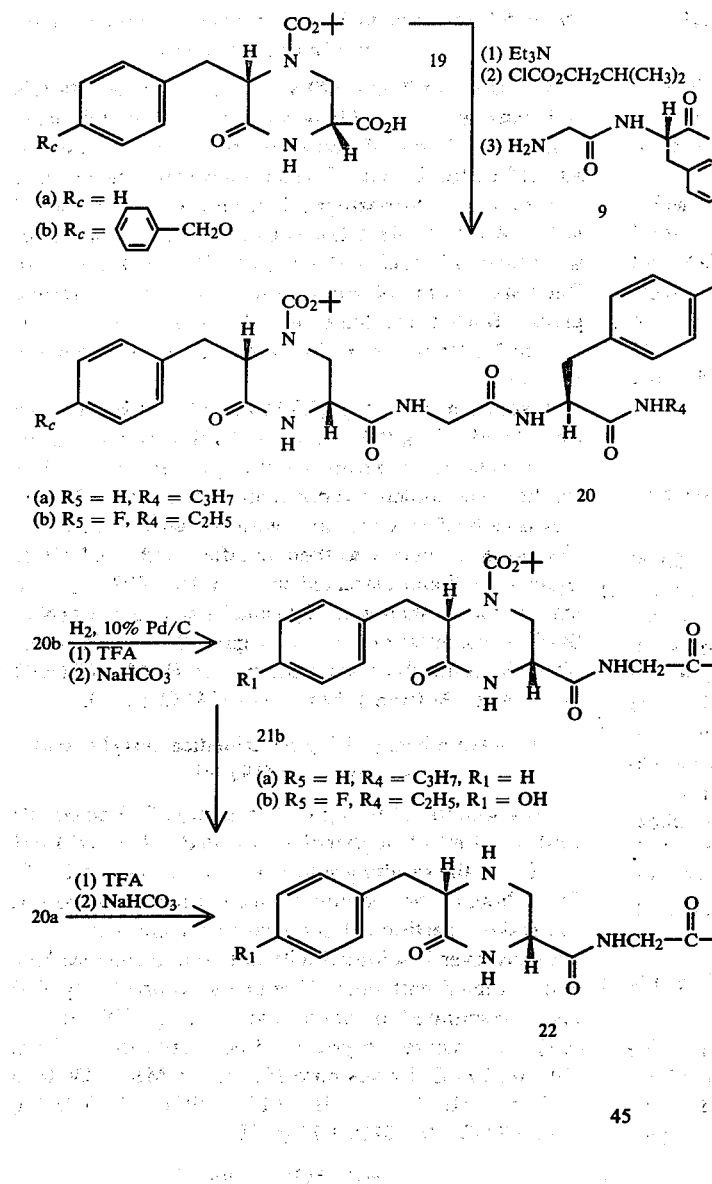
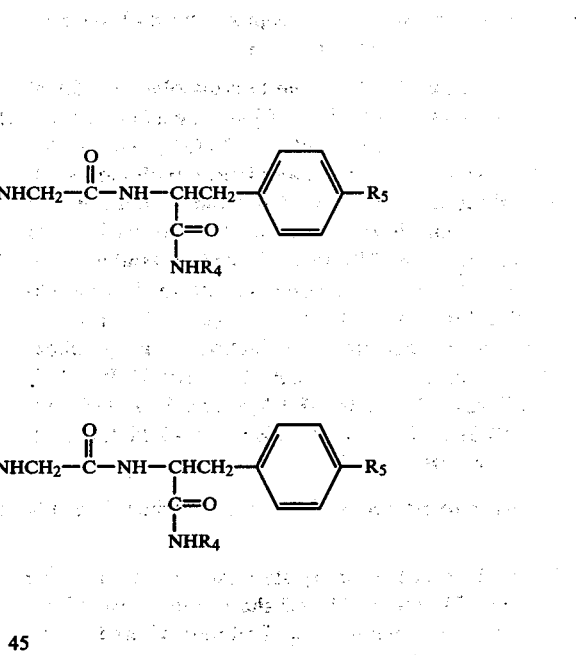

EXAMPLE 20a

Cis
$N^\alpha$-[N-[[4-t-Butoxycarbonyl)-6-oxo-5-benzyl-2-piperazinyl]carbonyl]glycyl]-N-propyl-L-phenylalaninamide (20a (cis))

1.67 g (5.00 mmole) of acid 19a (cis), is dissolved in 30 ml of sieve-dried THF under Ar and the stirred solution cooled in a CH$_3$OH/ice bath. 0.76 ml (5.5 mmole) of isobutyl chloroformate is added dropwise via syringe. After 10 minutes a freshly prepared solution of 1.65 g (5.5 mmole) of gly-phe-NHC$_3$H$_7$ hydrochloride 9c and 1.4 ml (10 mmole) of Et$_3$N in 50 ml THF and 7.5 ml H$_2$O is added in one portion. The ice bath is removed and stirring continued at 25° C. for 2 hours. The mixture is poured into H$_2$O and extracted twice with ether/CH$_2$Cl$_2$. The combined organic layers are washed twice with water and brine and dried (Na$_2$SO$_4$). Concentration in vacuo followed by column chromatography gives protected peptide 20a (cis).

EXAMPLE 20b

Cis
$N^\alpha$-[N-[[4-t-Butoxycarbonyl)-6-oxo-5-(4-benzyloxybenzyl)-2-piperazinyl]carbonyl]glycyl]-N-ethyl-4-fluorophenylalaninamide (20b (cis))

When in the procedure of Example 20a, 19b (cis) is substituted for 19a (cis) and 9b is substituted for 9c, the title compound is obtained.

EXAMPLE 21

Cis
$N^\alpha$-[N-[[4-(t-Butoxycarbonyl)-5-(4-Hydroxybenzyl)-6-oxo-2-piperazinyl]carbonyl]glycyl]-N-ethyl-4-fluorophenylalaninamide (21b (cis))

A mixture of 3.21 g (5.00 mole) of 20b (cis) dissolved in 100 ml of EtOH and 0.60 g of 10% Pd/C is shaken in a Parr hydrogenator (30 to 50 pd) until uptake of one equivalent of hydrogen ceases. The mixture is filtered through filter aid and the filter cake rinsed with EtOH. The filtrate is concentrated and dried under vacuum to give carbamate 21b (cis).

EXAMPLE 22a

Cis
N$^\alpha$-[N-[[5-Benzyl-6-oxo-2-piperazinyl]carbonyl]-glycyl]-N-propyl-L-phenylalaninamide (22a (cis))

2.45 g (5.00 mmole) of carbamate 20a (cis) is placed in a flask in an ice bath. 10 ml of TFA is added slowly with swirling and the ice bath removed. After 8 minutes the solution is poured into 200 ml of anhydrous ether. The supernatant is decanted and the salt washed with fresh anhydrous ether. Dilute aqueous NaHCO$_3$ is added and the mixture extracted twice with CH$_2$Cl$_2$. The extracts are washed with water, brine and dried (Na$_2$SO$_4$). Concentration in vacuo followed by chromatography on silica gel gives tetrapeptide 22a (cis).

trans
N$^\alpha$-[N-[[5-Benzyl-6-oxo-2-piperazinyl]carbonyl]-glycyl]-N-propyl-L-phenylalaninamide (22a (trans))

Substitution of 19a (trans) for 19a (cis) in the procedure of Example 20a and of the product thereof in the foregoing procedure, gives the title compound.

EXAMPLE 22b

Cis
N$^\alpha$-[N-[[5-(4-Hydroxybenzyl)-6-oxo-2-piperazinyl]carbonyl]glycyl]-N-ethyl-4-fluorophenylalaninamide (22b (cis))

When in the procedure of Example 22a, 21b (cis) is substituted for 20a (cis), the title compound is obtained.

trans
N$^\alpha$-[N-[[5-(4-Hydroxybenzyl)-6-oxo-2-piperazinyl]carbonyl]glycyl]-N-ethyl-4-fluorophenylalaninamide (22b (trans))

Substitution of 18b (trans) for 18a (trans) in the procedure of Example 19a and subsequently employing the product in the procedures of Examples 20b, 21 and 22a, gives the title compound.

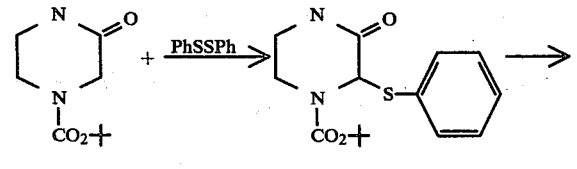

EXAMPLE 23 t-Butyl 3-oxo-2-phenylthio-1-piperazinecarboxylate (23)

To a solution of dry diisopropylamine (0.31 ml, 2.2 mmole) and dry THF (2 ml) at 0° C. under argon is added dropwise, a hexane solution of n-butyllithium (0.90 ml, 2.2 mmole). After ½ hour of stirring a solution of 2 (0.200 g, 1.00 mmole) in 5 ml of dry THF is added dropwise and stirring continued for 3 hours. A solution of diphenyldisulfide (0.240 g, 1.10 mmole) in dry THF was added dropwise and the mixture is stirred for 1 hour at 0° C. before being allowed to warm to room temperature. Stirring is continued overnight and the reaction is quenched into ether/water and the aqueous phase extracted twice with ether. The ethereal extracts are washed with brine and dried over Na$_2$SO$_4$, and the solvent is evaporated. The resulting yellow oil was chromatographed with 50% ethylacetate/chloroform and triturated with ether to afford 0.180 g (59%) of colorless solid 23. M.p. 138°–140° C. Alternatively, the phenyl ester of benzenesulfonothioic acid may be employed in place of diphenyldisulfide to prepare 23.

EXAMPLE 24

Methyl 4-(t-Butoxycarbonyl)-2-oxo-3-phenylthio-1-piperazineacetate (24)

When in the procedure of Example 4a, 23 is substituted for 3a, the title compound is produced.

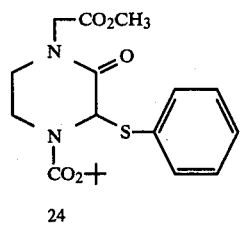

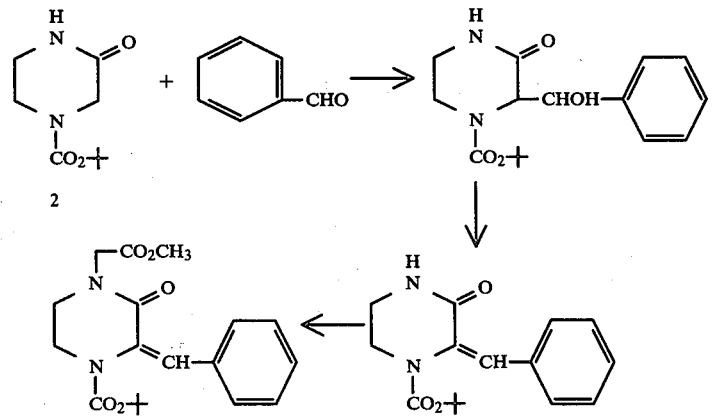

EXAMPLE 25 t-Butyl 3-oxo-2-benzylidenyl-1-piperazinecarboxylate (25)

To a solution of diisopropylamine (0.31 ml, 2.2 mmole) and dry THF (2 ml) at 0° C. under argon is added dropwise a hexane solution of n-butyllithium (0.90 ml, 2.2 mmole). After ½ hour, a solution of 2 (0.200 g, 1.00 mmole) in dry THF is added dropwise and stirred at 0° C. for 3 hours, and benzaldehyde (0.11 ml, 1.1 mmole) added dropwise. The reaction is stirred for 1 hour, the cooling bath is removed and the reaction stirred for an additional 2 hours. Acetyl chloride (0.078 ml, 1.1 mmole) was added and the mixture stirred overnight, quenched into ether/water, and purified as described in Example 23. Chromatography on silica gel with 10% methanol/chloroform yields colorless solid 25. M.p. 191°–193° C.

EXAMPLE 26

Methyl 4-(t-Butoxycarbonyl)-2-oxo-3-benzylidenyl-1-piperazineacetate (26)

When in the procedure of Example 4a, 25 is substituted for 3a, the title compound is obtained.

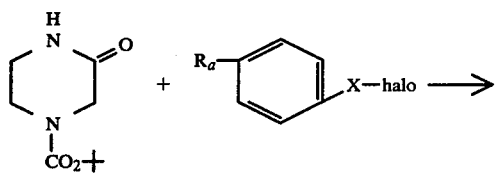

(a) X = S, $R_a$ = Cl
(b) X = SO, $R_a$ = H
(c) X = SO$_2$, $R_a$ = H
(d) X = CO, $R_a$ = H

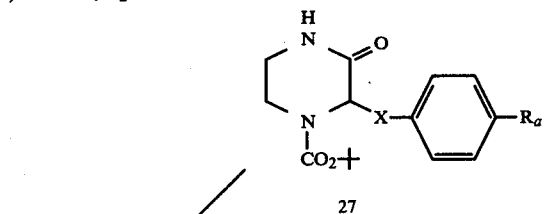

27

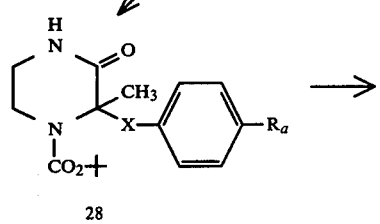

28

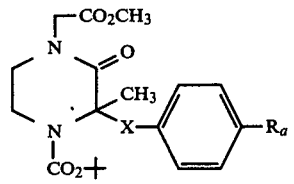

29

EXAMPLE 27a t-Butyl 2-(4-Chlorophenylthio)-3-oxo-1-piperazinecarboxylate (27a)

When in the procedure of Example 3a, (4-chlorophenyl)sulfenyl chloride is substituted for p-benzyloxybenzyl chloride, the title compound is obtained.

EXAMPLE 27b t-Butyl 2-phenylsulfinyl-3-oxo-1-piperazinecarboxylate (27b)

When in the procedure of Example 3a, benzenesulfinylchloride is substituted for p-benzyloxybenzyl chloride, the title compound is obtained.

EXAMPLE 27c t-Butyl 2-phenylsulfonyl-3-oxo-1-piperazinecarboxylate (27c)

When in the procedure of Example 3a, benzenesulfonyl bromide is substituted for p-benzyloxybenzyl chloride, the title compound is obtained.

EXAMPLE 27d t-Butyl 2-Benzoyl-3-oxo-1-piperazinecarboxylate (27d)

When in the procedure of Example 3a, benzoyl chloride is substituted for p-benzyloxybenzyl chloride, the title compound is obtained.

Alternatively, ethyl benzoate may be substituted for p-benzyloxybenzyl chloride to give 27d.

EXAMPLE 28a t-Butyl 2-(4-chlorophenylthio)-2-methyl-3-oxo-1-piperazinecarboxylate (28a)

When in the procedure of Example 3a, 27a is substituted for 2 and methyl iodide substituted for p-benzyloxybenzyl chloride, the title compound is obtained.

EXAMPLE 28b t-Butyl 2-phenylsulfinyl-2-methyl-3-oxo-1-piperazinecarboxylate (28b)

When in the procedure of Example 3a, methyl iodide is substituted for p-benzyloxybenzyl chloride and 27b is substituted for 2, the title compound is obtained.

EXAMPLE 28c t-Butyl 2-phenylsulfonyl-2-methyl-3-oxo-1-piperazinecarboxylate (28c)

When in the procedure of Example 3a, methyl iodide is substituted for p-benzyloxybenzyl chloride, and 27c is substituted for 2, the title compound is obtained.

EXAMPLE 28d t-Butyl 2-benzoyl-2-methyl-3-oxo-1-piperazinecarboxylate (28d)

When in the procedure of Example 3a, methyl iodide is substituted for p-benzyloxybenzyl chloride and 27d is substituted for 2, the title compound is obtained.

EXAMPLE 29a

Methyl 4-(t-butoxycarbonyl)-2-oxo-3-(4-chlorophenylthio)3-methyl-1-piperazineacetate (29a)

When in the procedure of Example 4a, 28a is substituted for 3a, the title compound is obtained.

EXAMPLE 29b

Methyl 4-(t-butoxycarbonyl)-2-oxo-3-phenylsulfinyl-3-methyl-1-piperazineacetate (29b)

When in the procedure of Example 4a, 28b is substituted for 3a, the title compound is obtained.

EXAMPLE 29c

Methyl 4-(t-butoxycarbonyl)-2-oxo-3-phenylsulfonyl-3-methyl-1-piperazineacetate (29c)

When in the procedure of Example 4a, 28c is substituted for 3a, the title compound is obtained.

EXAMPLE 29d

Methyl 4-(t-butoxycarbonyl)-2-oxo-3-benzoyl-3-methyl-1-piperazineacetate (29d)

When in the procedure of Example 4a, 28d is substituted for 3a, the title compound is obtained.

EXAMPLE 30

$N^\alpha$-[N[[4-(t-butoxycarbonyl)-2-oxo-3-benzoyl-3-methyl-1-piperazinyl]-acetyl]-glycyl]-N-methyl-L-phenylalaninamide (30)

When in the procedure of Example 5a, 29d is substituted for 4a, and the product subjected to the procedure of Example 10a, the title compound is obtained.

EXAMPLE 31

$N^\alpha$-[N-[[3-Benzoyl-3-methyl-2-oxo-1-piperazinyl]acetyl]-glycyl]-N-methyl-L-phenylalaninamide (31)

When in the procedure of Example 12a, 30 is substituted for 11a, the title compound is obtained.

EXAMPLE 32

$N^\alpha$-[N-[[3-$\alpha$-hydroxybenzyl)-3-methyl-2-oxo-1-piperazinyl]-acetyl]glycyl]-N-methyl-L-phenylalaninamide (32)

To a methanol solution of 31 (4.5 g, 10 mmole) sodium borohydride (0.75 g, 20 mmole) is added, and the mixture is stirred at room temperature for 4 hours. The solvent is removed in vacuo and the residue triturated with water and extracted into chloroform. The extract is washed with brine and dried over $Na_2SO_4$ and the solvent evaporated to give 32.

Similarly, esters of formulae 24, 26, 29a, 29b and 29c may be hydrolyzed to the free acid and coupled with polypeptides of general Formula IV to yield compounds of general Formula I.

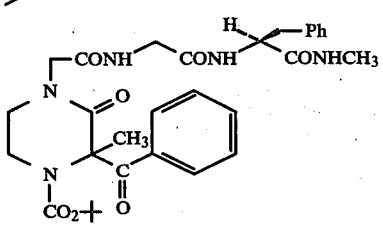

30

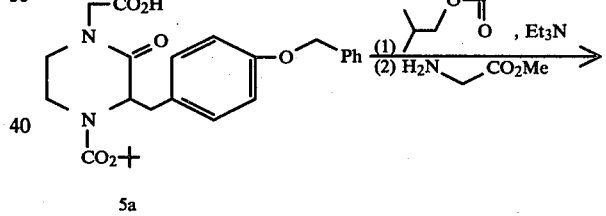

5a

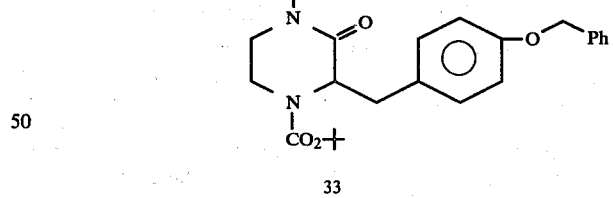

33

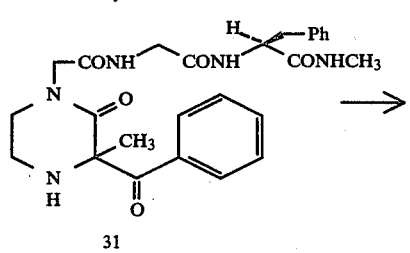

31

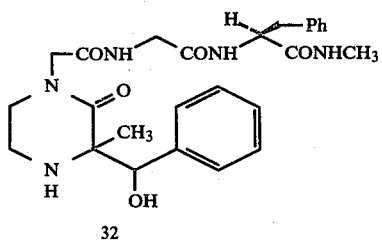

32

EXAMPLE 33

N-[[4-t-Butoxycarbonyl-3-(benzyloxybenzyl)-2-oxo-1-piperazinyl]acetyl]glycine methyl ester (33)

To a solution of 5a (0.2282 g, 0.50 mmole) in dry THF was added triethylamine (0.077 ml, 0.55 mmole). The mixture was cooled to $-10°$ C. to $-15°$ C. and isobutylchloroformate (0.072 ml, 0.55 mmole) added by syringe. After 10 minutes, a freshly neutralized solution of glycine methyl ester hydrochloride (0.189 g, 1.51 mmole), water, THF, and triethylamine is added. The cooling bath is removed and the mixture reacted at room temperature for 4 hours. The solution is quenched into ether/0.5M HCl solution. The aqueous phase is extracted with ether and chloroform and the organic extracts washed with saturated aqueous NaHCO$_3$, dried over Na$_2$SO$_4$, and evaporated to dryness to give 33, which was shown to be homogeneous by TLC on silica gel plates, and the structure corroborated by NMR. NMR (CDCl$_3$) δ 1.30 (s, 9, t-boc), 3.14 (d, 2, benzylic methylene), 3.68 (s, 3, ester), 3.8–4.3 (m, 8, methylenes), 4.70 (t-1, C$_3$-H), 4.98 (s, 2, benzyloxy methylene), 6.92 (q, 5, aromatic and amide NH), 7.31 (s, 5, aromatic).

By hydrolyzing the ester 33, repeating the abovedescribed procedure using the resulting protected piperazinoneacetylglycine and an ester of phenylalanine, and reacting the product thereof with methylamine, 10a may be obtained.

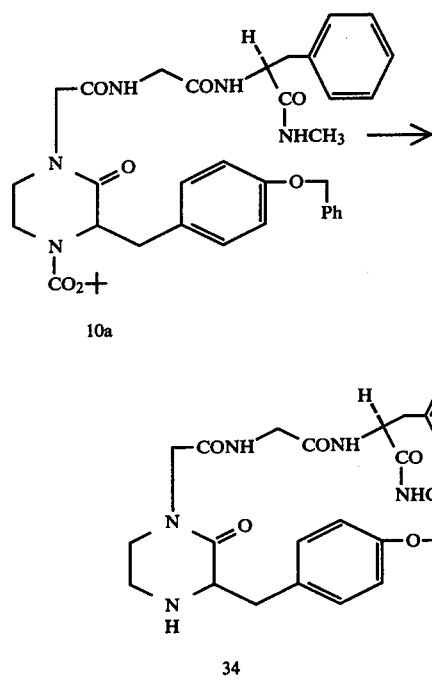

EXAMPLE 34

N$^\alpha$-[N-[[3-(4-Benzyloxybenzyl-2-oxo-1-piperazinyl)]acetyl]glycyl]-N-methyl-L-phenylalaninamide (34)

To the diprotected-pseudo-tetrapeptide, 10a, (0.65 g. 9.7×10$^{-4}$ mmole) was added trifluoroacetic acid (8 ml). The mixture was stirred for 20 minutes and the solvent was then evaporated. The concentrate was dissolved in CH$_2$Cl$_2$ and was then washed with saturated aqueous NaHCO$_3$. The alkaline washings were back extracted with CH$_2$Cl$_2$. The CH$_2$Cl$_2$ extracts were combined and washed with saturated aqueous NaCl before being dried over Na$_2$SO$_4$. Filtration of the drying agent and evaporation of the filtrate gave an almost colorless foam which was purified by preparative layer chromatography (12% CH$_3$OH/CHCl$_3$) affording 34 as a colorless foam, 0.33 g (60%), shown by TLC as a homogeneous product lacking 10a. NMR (CDCl$_3$) δ 2.30 (broad s, 1, amine NH), 2.65 (d, 3, methyl amide), 2.8–4.1 (m, 13, methylenes), 4.68 (m, 1, phenylalanine methine), 4.99 (s, 2, benzyloxy methylene), 6.7–7.7 (m, 17, aromatic and amide NH's).

The phenol protected pseudo-tetrapeptide, 34, (0.20 g, 3.5×10$^{-4}$ mmole) was dissolved in 60% aqueous acetic acid (8 ml) and hydrogenated at 40 psi using 10% Pd/C (0.05 g) as a catalyst. After 5 hours, the catalyst was removed by filtration through a pad of Celite and the filtrate was evaporated to a colorless solid. This was dissolved in EtOAc and the organic solution was then washed with saturated aqueous NaHCO$_3$. The alkaline washings were back extracted with EtOAc. The EtOAc extracts were combined and dried over Na$_2$SO$_4$. Filtration of the drying agent and evaporation of the filtrate gave a foam which was purified by preparative layer chromatography (20% CH$_3$OH/CHCl$_3$) affording 12a as a colorless foam: 0.12 g (71%).

This product was identical in all respects to that isolated via the alternative deprotection sequence described in Examples 11 and 12a.

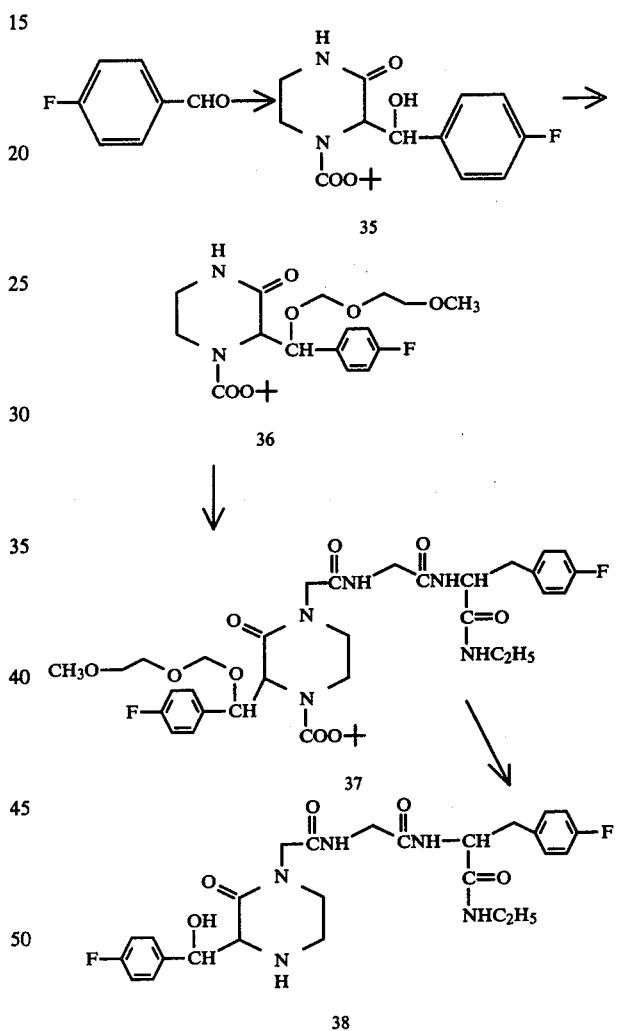

EXAMPLE 35 t-Butyl 3-Oxo-2-(α-hydroxy-4-fluorobenzyl)-1-piperazine carboxylate (35)

To a solution of diisopropylamine (3.1 ml, 22 mmole) and dry THF (5 ml) at 0° C. under argon is added dropwise a hexane solution of n-butyllithium (13.8 ml, 22 mmole). After ¾ hour, a solution of 2 (2.0 g, 10 mmole) in 75 ml of dry THF is added dropwise and stirred at 0° C. for 3 hours and 4-fluoro-benzaldehyde (13.6 g, 11 mmole) added dropwise. The reaction mixture was stirred at room temperature for 68 hours, poured into water, and extracted into ether. The extract was washed with brine, dried over MgSO₄, and concentrated under reduced pressure, and the residue recrystallized from ethanol to give 35. M.p. 219° C. (dec.).

EXAMPLE 36 t-Butyl 3-Oxo-2-(α-(2-methoxyethoxy)methoxy-4-fluorobenzyl)-1-piperazine carboxylate (36)

To 0.13 g (0.0054 mole) of NaH (0.22 g of a 61% dispersion in oil, washed with hexane) in 10 ml of dimethylformamide (DMF) was added 1.6 g of 35 in 20 ml of dry DMF, and the mixture stirred at 0° C. for 30 minutes. A solution of 0.67 g (0.0055 mole) of (2-methoxyethoxy)methyl chloride in 5 ml of dry DMF was added and the mixture allowed to warm to room temperature, stirred for 1 hour, and poured into 50 ml of water. The product was extracted into ethyl acetate and the extract washed with brine and dried over MgSO₄. After filtration, the solvent was removed at reduced pressure and the residue triturated with hexane and filtered to give the title compound.

EXAMPLE 37

Nα-[N-[[4-(t-Butoxycarbonyl)-2-oxo-3-(α-(2-methoxyethoxy)methoxy)-4-fluorobenzyl]-1-piperazinyl]acetyl]-glycyl]-N-ethyl-4-fluorophenylalaninamide (37)

When in the procedure of Example 4a, 36 is substituted for 3a, and the product subjected to the procedures of Examples 5a and 10b, the title compound is obtained.

EXAMPLE 38

Nα-[N-[[2-Oxo-3-(α-hydroxy-4-fluorobenzyl)-1-piperazinyl]acetyl]glycyl]-N-ethyl-4-fluorophenylalaninamide (38)

Compound 37, produced above, is dissolved in an excess of cold trifluoroacetic acid and stirred at 0° C. for ½ hour to give 38 trifluoroacetate. This salt is dissolved in dilute aqueous sodium hydroxide and extracted into ethyl acetate and the extract concentrated under reduced pressure. Recrystallization from ethyl acetate/hexane gives 38.

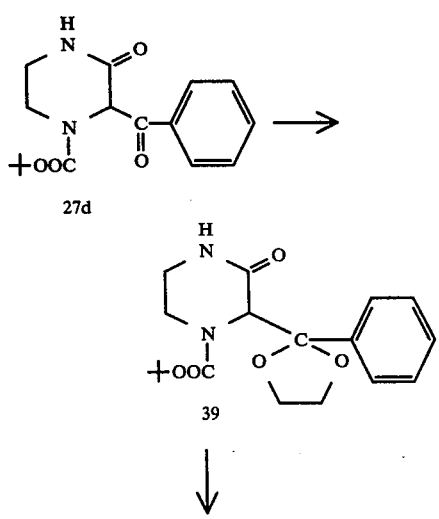

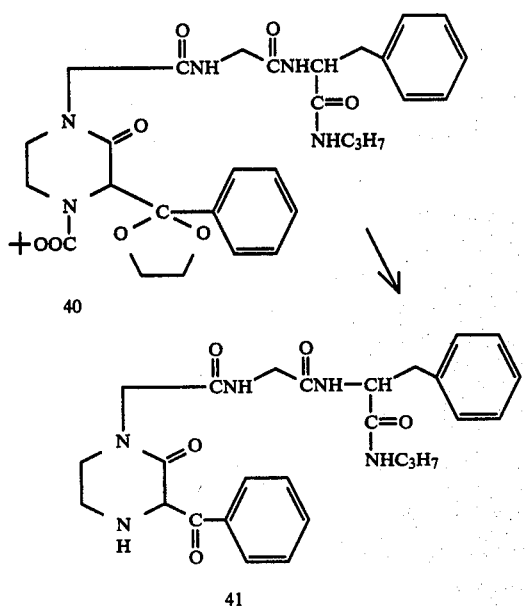

EXAMPLE 39 t-Butyl 3-Oxo-2-(α-ethylenedioxybenzyl)-1-piperazine carboxylate (39)

A mixture of 2.0 g (6.5 mmole) of 27d, 1.25 g (20.0 mmole) of ethyleneglycol, and 1.0 g of p-toluenesulfonic acid monohydrate is refluxed in 50 ml of benzene in a Dean-Stark apparatus until the collection of water ceases. The reaction mixture is cooled, washed with saturated NaHCO₃ solution and brine, dried over MgSO₄, and filtered. The filtrate is stirred with 2.2 g (10 mmole) of di-t-butyldicarbonate at reflux temperature and then concentrated to a solid residue and recrystallized from benzene/hexane to yield the title compound.

EXAMPLE 40

Nα-[N-[[4-(t-Butoxycarbonyl)-2-oxo-3-(α-ethylenedioxybenzyl)-1-piperazinyl]acetyl]glycyl]-N-propylphenylalaninamide (40)

When in the procedure of Example 4a, 39 is substituted for 3a, and the product subjected to the procedures of Examples 5a and 10a, with the substitution of 9c for 9a, the title compound is produced.

EXAMPLE 41

Nα-[N-[(2-Oxo-3-benzoyl-1-piperazinyl)acetyl]glycyl]-N-propylphenylalaninamide (41)

A mixture of 1.0 g of 40 and 10 ml of 2M hydrochloric acid in 10 ml of ethanol is stirred at room temperature for 2 hours. The mixture is made alkaline with 10% NaOH solution and extracted into ethyl acetate. After being washed with brine and dried over MgSO₄, the extract is concentrated to give the title compound.

We claim:
1. A compound of the formula

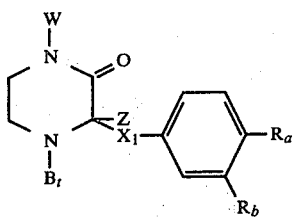

wherein W is $CH_2COOH$, $CH_2COOR$ or hydrogen, R is straight or branched chain lower alkyl having from 1 to 4 carbon atoms, Z is hydrogen or straight chain lower alkyl having from 1 to 4 carbon atoms and $X_1$ is methylene, carbonyl, hydroxymethylene, thio, blocked carbonyl, wherein blocked carbonyl is selected from the group consisting of $C_{2-3}$ alkylene ketal and $C_{1-4}$ dialkyl hydrazone, or blocked hydroxymethylene, wherein the hydroxy blocking group is selected from the group consisting of benzyl, methyl, tertiary butoxy carbonyl, $C_{1-4}$ trialkylsilyl, methoxymethyl, (2-methoxyethoxy)methyl and tetrahydropyranyl, sulfinyl or sulfonyl, with the proviso that when X is sulfinyl or sulfonyl, Z is other than H, or $X_1$ and Z, taken together, are methylidenyl, $R_a$ is hydrogen, halogen or protected hydroxy and $R_b$ is hydrogen or $R_a$ and $R_b$ are protected hydroxy, wherein protected hydroxy comprises a hydroxy moiety blocked by a hydroxy blocking group selected from the group defined above, and $B_t$ is a $C_{4-5}$ tertiary-alkoxycarbonyl blocking group, with the proviso that when W is hydrogen and $X_1$ is methylene, $R_a$ is halogen and with the additional proviso that when W is hydrogen and $X_1$ and Z, taken together, are methylidenyl, $R_a$ is other than hydrogen.

2. A compound of claim 1 wherein $X_1$ is methylene.
3. A compound of claim 1 wherein $X_1$ is carbonyl.
4. A compound of claim 1 wherein $X_1$ is hydroxymethylene.
5. A compound of claim 1 wherein Z is hydrogen.
6. A compound of claim 1 wherein W is hydrogen.

* * * * *